(12) United States Patent
Gross et al.

(10) Patent No.: US 8,633,209 B2
(45) Date of Patent: Jan. 21, 2014

(54) HYDROBROMIDE SALTS OF A PYRAZOLYLAMINOQUINAZOLINE

(75) Inventors: Timothy David Gross, San Diego, CA (US); Patrick B. O'Donnell, San Diego, CA (US)

(73) Assignee: Ambit Biosciences Corporation, San Diego, CA (US)

( * ) Notice: Subject to any disclaimer, the term of this patent is extended or adjusted under 35 U.S.C. 154(b) by 0 days.

(21) Appl. No.: 13/223,118

(22) Filed: Aug. 31, 2011

(65) Prior Publication Data

US 2012/0053195 A1 Mar. 1, 2012

Related U.S. Application Data

(60) Provisional application No. 61/379,291, filed on Sep. 1, 2010.

(51) Int. Cl.
- *A01N 43/54* (2006.01)
- *A61K 31/517* (2006.01)
- *C07D 239/72* (2006.01)
- *C07D 401/00* (2006.01)

(52) U.S. Cl.
USPC ............ 514/266.2; 514/266.1; 544/283; 544/284; 544/285; 548/358.1

(58) Field of Classification Search
USPC ............ 544/283, 284, 285; 548/358.1; 514/266.1, 266.2
See application file for complete search history.

(56) References Cited

U.S. PATENT DOCUMENTS

2005/0038023 A1 2/2005 Bebbington et al.
2010/0317659 A1* 12/2010 Abraham et al. .......... 514/234.5

FOREIGN PATENT DOCUMENTS

WO 2010099379 A1 9/2010

OTHER PUBLICATIONS

Chemburkar et al., "Dealing with the impact of ritonavir polymorphs on the late stages of bulk drug process development," Org. Process Res. Dev. 2000, 4, 413-417.
Vainchenker et al., "JAKs in pathology: role of Janus kinases in hematopoietic malignancies and immunodeficiencies," Sem. Cell. Dev. Biol. 2008, 19, 385-393.
Vippagunta et al., "Crystalline solids," Adv. Drug Deliv. Rev. 2001, 48, 3-26.
Yamaoka et al., "The Janus kinases (Jaks)," Genome Biol. 2004, 5, 253.1-253.6.
Yu, "Amorphous pharmaceutical solids: preparation, characterization and stabilization," Adv. Drug Deliv. Rev. 2001, 48, 27-42.
Peterson et al., "Expanding the scope of crystal form evaluation in pharmaceutical science," J. Pharm. Pharmaceut. Sci., 2006, 9, 317-326.
Bernstein, "Crystal structure prediction and polymorphism," ACA Transactions 2004, 39, 14-23.

* cited by examiner

*Primary Examiner* — Paul V Ward
(74) *Attorney, Agent, or Firm* — Jones Day

(57) ABSTRACT

Provided herein are hydrobromide salts of a pyrazolylaminoquinazoline, and pharmaceutical compositions thereof. Also provided are methods of their use for treating, preventing, or ameliorating a proliferative disease.

27 Claims, 6 Drawing Sheets

HYDROBROMIDE SALTS OF A PYRAZOLYLAMINOQUINAZOLINE

CROSS REFERENCE TO RELATED APPLICATIONS

This application claims the benefit of the priority of U.S. Provisional Application No. 61/379,291, filed Sep. 1, 2010, the disclosure of which is incorporated herein by reference in its entirety.

FIELD

Provided herein are hydrobromide salts of a pyrazolylaminoquinazoline, and pharmaceutical compositions thereof. Also provided are methods of their use for treating, preventing, or ameliorating a proliferative disease.

BACKGROUND

Janus kinase (JAK) is a family of intracellular non-receptor tyrosine kinases for cytokine receptor signaling in blood formation and immune responses, which is comprised of Janus kinase 1 (JAK1), Janus kinase 2 (JAK2), Janus kinase 3 (JAK3), and tyrosin kinase 2 (TYK2) (Yamaoka et al., Genome Biol. 2004, 5, 253). The JAK kinases are implicated in myeloproliferative disorders, cancers, including blood borne and solid tumors, and immunodeficiency (Vainchenker et al., Sem. Cell Dev. Biol. 2008, 19, 385-393). Exemplary disorders include chronic myeloid leukemia (CML), polycythemia vera (PV), essential thrombocythemia (ET), primary myelofibrosis (PMF), chronic eosinophilic leukemia (CEL), chronic myelomonocytic leukemia (CMML), and systemic mastocytosis (SM). Myeloproliferative disorders are believed to arise from either gain-of-function mutations to JAK itself or from activation by the oncoprotein BCR-ABL, which specifically activates the JAK2 pathway. For example, mutations and translocations in the JAK genes leading to constitutively active JAK proteins are associated with a variety of hematopoietic malignancies, including the myeloproliferative disorders (JAK2), acute lymphoblastic leukemia (JAK2), acute myeloid leukemia (JAK2, JAK1), acute megakaryoblastic leukemia (JAK2, JAK3) and T-cell precursor acute lymphoblastic leukemia (JAK1) (Vainchenker et al., Sem. Cell Dev. Biol. 2008, 19, 385-393). In contrast, loss-of-function mutations of JAK3 and TYK2 lead to immunodeficiency (Vainchenker et al., Sem. Cell Dev. Biol. 2008, 19, 385-393). Therefore, there is a need for JAK inhibitors as therapeutic agents for treating JAK-mediated disorders or diseases.

SUMMARY OF THE DISCLOSURE

Provided herein is a hydrobromide salt of (4-fluorophenyl)(4-(5-methyl-1H-pyrazol-3-ylamino)quinazolin-2-yl) methanol, or a hydrate or pharmaceutically acceptable solvate thereof. In one embodiment, the hydrobromide salt is crystalline. In another embodiment, the hydrobromide salt is solvated. In yet another embodiment, the hydrobromide salt is unsolvated.

In another embodiment, provided herein are polymorphs of a hydrobromide salt of (4-fluorophenyl)(4-(5-methyl-1H-pyrazol-3-ylamino)quinazolin-2-yl)methanol, or a hydrate or pharmaceutically acceptable solvate thereof. In one embodiment, the hydrobromide salt is a crystalline. In one embodiment, the crystalline hydrobromide salt is unsolvated. In another embodiment, the crystalline hydrobromide salt is solvated.

Further provided herein is crystalline Form A of a hydrobromide salt of (4-fluorophenyl)(4-(5-methyl-1H-pyrazol-3-ylamino)quinazolin-2-yl)methanol. In one embodiment, the crystalline Form A is unsolvated.

In one embodiment, provided herein is crystalline Form B of a hydrobromide salt of (4-fluorophenyl)(4-(5-methyl-1H-pyrazol-3-ylamino)quinazolin-2-yl)methanol.

In one embodiment, provided herein is crystalline Form C of a hydrobromide salt of (4-fluorophenyl)(4-(5-methyl-1H-pyrazol-3-ylamino)quinazolin-2-yl)methanol. In one embodiment, the crystalline Form C is solvated. In another embodiment, the solvent in the crystalline Form C is toluene. In yet another embodiment, crystalline Form C contains about 0.4 moles of toluene per mole of 4-fluorophenyl)(4-(5-methyl-1H-pyrazol-3-ylamino)quinazolin-2-yl)methanol.

In one embodiment, provided herein is crystalline Form D of a hydrobromide salt of (4-fluorophenyl)(4-(5-methyl-1H-pyrazol-3-ylamino)quinazolin-2-yl)methanol.

In one embodiment, provided herein is crystalline Form E of a hydrobromide salt of (4-fluorophenyl)(4-(5-methyl-1H-pyrazol-3-ylamino)quinazolin-2-yl)methanol.

In one embodiment, provided herein is crystalline Form F of a hydrobromide salt of (4-fluorophenyl)(4-(5-methyl-1H-pyrazol-3-ylamino)quinazolin-2-yl)methanol.

In one embodiment, provided herein is a pharmaceutical composition, comprising a hydrobromide salt of (4-fluorophenyl)(4-(5-methyl-1H-pyrazol-3-ylamino)quinazolin-2-yl)methanol, or a hydrate or pharmaceutically acceptable solvate thereof, or a crystalline form thereof, including Forms A, B, C, D, E, and F; and one or more pharmaceutically acceptable excipients.

In one embodiment, provided herein is a method of treating a proliferative disease in a subject, comprising administering to the subject a hydrobromide salt of (4-fluorophenyl)(4-(5-methyl-1H-pyrazol-3-ylamino)quinazolin-2-yl)methanol, or a hydrate or pharmaceutically acceptable solvate thereof, or a crystalline form thereof, including Forms A, B, C, D, E, and F.

In one embodiment, provided herein is a method of treating, preventing, or ameliorating a JAK-mediated condition, disorder, or disease in a subject, comprising administering to the subject a hydrobromide salt of (4-fluorophenyl)(4-(5-methyl-1H-pyrazol-3-ylamino)quinazolin-2-yl)methanol, or a hydrate or pharmaceutically acceptable solvate thereof, or a crystalline form thereof, including Forms A, B, C, D, E, and F.

In one embodiment, provided herein is a method of inhibiting the growth of a cell, comprising contacting the cell with a hydrobromide salt of (4-fluorophenyl)(4-(5-methyl-1H-pyrazol-3-ylamino)quinazolin-2-yl)methanol, or a hydrate or pharmaceutically acceptable solvate thereof, or a crystalline form thereof, including Forms A, B, C, D, E, and F.

In one embodiment, provided herein is a method of modulating the activity of a JAK kinase, comprising contacting the JAK kinase with a hydrobromide salt of (4-fluorophenyl)(4-(5-methyl-1H-pyrazol-3-ylamino)quinazolin-2-yl)methanol, or a hydrate or pharmaceutically acceptable solvate thereof, or a crystalline form thereof, including Forms A, B, C, D, E, and F.

DETAILED DESCRIPTION

Figure 1:
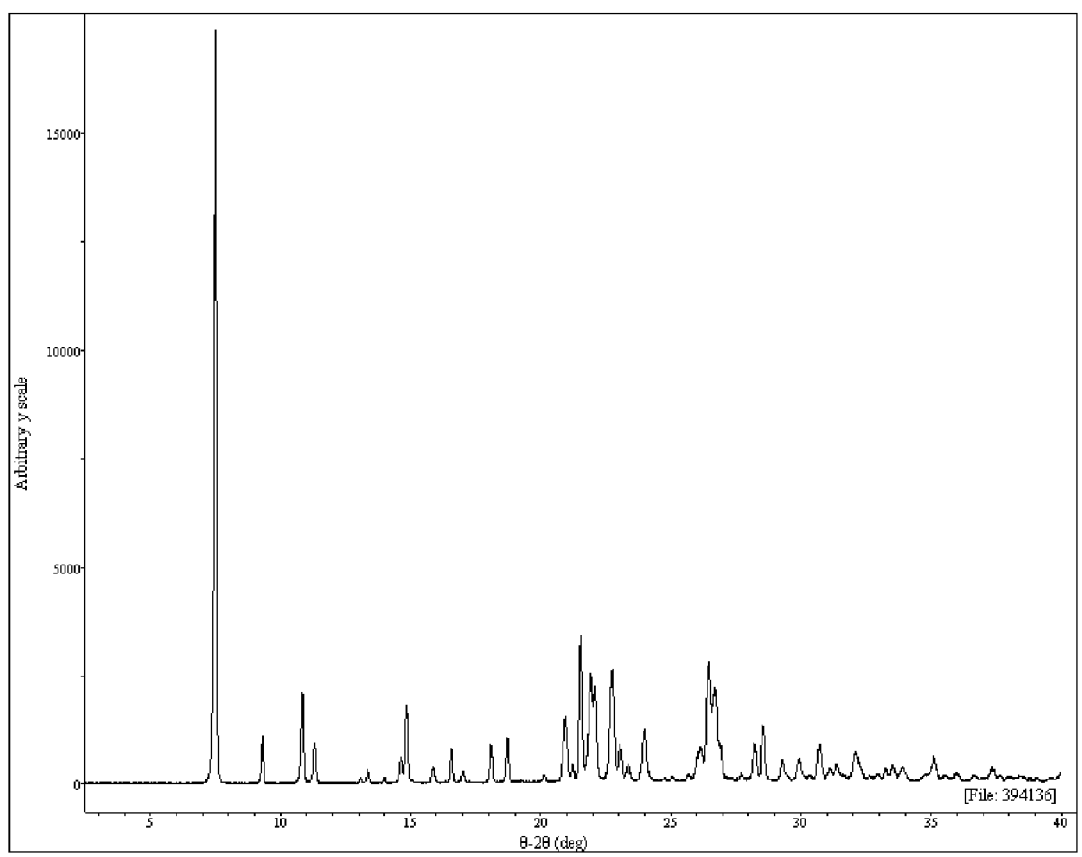
FIG. 1 depicts an X-ray powder (XRP) diffractogram of a hydrobromide salt of (4-fluorophenyl)(4-(5-methyl-1H-pyrazol-3-ylamino)quinazolin-2-yl)methanol in crystalline Form A.

To facilitate understanding of the disclosure set forth herein, a number of terms are defined below.

Generally, the nomenclature used herein and the laboratory procedures in organic chemistry, medicinal chemistry, physical chemistry, biochemistry, biology, pharmacology, and others described herein are those well known and commonly employed in the art. Unless defined otherwise, all technical and scientific terms used herein generally have the same meaning as commonly understood by one of ordinary skill in the art to which this disclosure belongs.

The term "tumor," "neoplasm," and "neoplastic disorder or disease" are used interchangeably herein and are meant to refer to unwanted cell proliferation of one or more subset of cells in a multicellular organism resulting in harm (i.e., discomfort or decreased life expectancy) to the multicellular organisms. In certain embodiments, a tumor can be benign (non-invasive) or malignant (invasive).

The term "cancer" is meant to refer to a malignant neoplasm, which is characterized by uncontrolled cell proliferation where cells have lost their normal regulatory controls that would otherwise govern the rate of cell growth. These unregulated, dividing cells can spread throughout the body and invade normal tissues in a process referred to as "metastasis."

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The term "therapeutically effective amount" is meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; and *Pharmaceutical Preformulation and Formulation,* 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "solvate" refers to a complex or aggregate formed by one or more molecules of a solute, e.g., a compound provided herein, and one or more molecules of a solvent, which is present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "JAK" or "Just Another Kinase" refers to a Janus kinase or a variant thereof, including, but not limited to, Janus kinase 1 (JAK1), Janus kinase 2 (JAK2), Janus kinase 3 (JAK3), and tyrosine kinase 2 (TYK2). JAK variants include proteins substantially homologous to a native JAK, i.e., proteins having one or more naturally or non-naturally occurring amino acid deletions, insertions or substitutions (e.g., JAK derivatives, homologs and fragments), as compared to the amino acid sequence of a native JAK. The amino acid sequence of a JAK variant is at least about 80% identical, at least about 90% identical, or at least about 95% identical to a native JAK.

The terms "JAK-mediated condition, disorder or disease" and "a condition, disorder, or disease mediated by JAK" refer to a condition, disorder, or disease characterized by abnormal or dysregulated, e.g., greater than normal, JAK activity. Abnormal JAK functional activity might arise as the result of JAK overexpression in cells, expression of JAK in cells which normally do not express JAK, or dysregulation due to constitutive activation, caused, for example, by a mutation in JAK. A JAK-mediated condition, disorder, or disease may be completely or partially mediated by inappropriate JAK activity. In particular, a JAK-mediated condition, disorder, or disease is one in which modulation of a JAK activity results in some effect on the underlying condition, disorder, or disease, e.g., a JAK inhibitor results in some improvement in at least some of patients being treated.

Hydrobromide Salts of a Pyrazolylaminoquinazoline

The selection of a solid form of a pharmaceutical compound is complex, given that different solid forms of the same pharmaceutical compound may have different physical and chemical properties, which may affect processing ability, stability, and/or bioavailability of the pharmaceutical compound. Potential pharmaceutical solid forms include amorphous and crystalline solid forms. Amorphous solid forms are characterized by a lack of long-range structural order, whereas crystalline solid forms are characterized by structural periodicity. Amorphous solid forms are sometimes selected because of their enhanced dissolution profiles, while crystalline solids are sometimes selected because of physical and/or chemical stability (Vippagunta et al., *Adv. Drug. Deliv. Rev.* 2001, 48, 3-26; Yu, *Adv. Drug. Deliv. Rev.* 2001, 48, 27-42).

Whether amorphous or crystalline, potential solid forms of a pharmaceutical compound include single-component and multiple-component solids. A single-component solid consists of the pharmaceutical compound in the absence of other compounds. Variety among single-component crystalline materials may potentially arise from the phenomenon of polymorphism, wherein multiple three-dimensional arrangements exist for a particular pharmaceutical compound (Byrn et al., *Solid State Chemistry of Drugs*, SSCI, West Lafayette, 1999). The importance of polymorphism in pharmaceutical development and drug discovery was underscored by the development of Ritonavir, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (Chemburkar et al., *Org. Process Res. Dev.* 2000, 4, 413-417).

Additional diversity among the potential solid forms of a pharmaceutical compound may arise from the possibility of multiple-component solids. Examples of multiple-component solids of a pharmaceutical compound include, but are not limited to, solids of pharmaceutically acceptable salts of the pharmaceutical compound; and solids of pharmaceutically acceptable solvates, hydrates, co-crystals, and clathrates of the pharmaceutical compound and its pharmaceutically acceptable salts. Moreover, multiple-component crystal forms may also be susceptible to polymorphism, wherein a given multiple-component composition may exist in more than one three-dimensional crystalline arrangement. The discovery of solid forms for a given pharmaceutical compound is important in the development of a safe, effective, stable, and marketable pharmaceutical compound.

In one embodiment, provided herein is a hydrobromide salt of (4-fluorophenyl)(4-(5-methyl-1H-pyrazol-3-ylamino)quinazolin-2-yl)methanol, having the structure of Formula I:

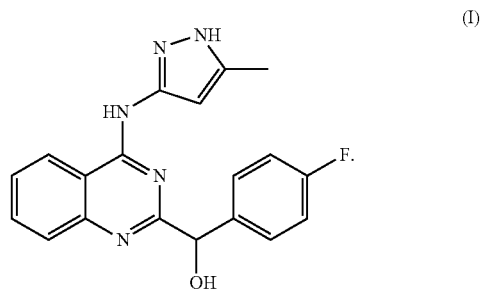 [SMILES: Cc1cc(Nc2nc(C(O)c3ccc(F)cc3)nc3ccccc23)n[nH]1]

(I)

The compound of Formula I has been identified as a JAK kinase inhibitor and can be prepared according to U.S. application Ser. No. 12/714,323, filed on Feb. 26, 2010 published as US 2010/0317659 on Dec. 16, 2010, the disclosure of which is incorporated by reference in its entirety.

In one embodiment, provided herein is a hydrobromide salt of (4-fluorophenyl)(4-(5-methyl-1H-pyrazol-3-ylamino)quinazolin-2-yl)methanol, or a hydrate or pharmaceutically acceptable solvate thereof. As used herein, the term "hydrobromide salt" is used interchangeably with the term "hydrobromic acid salt."

In one embodiment, the hydrobromide salt is unsolvated. In another embodiment, the hydrobromide salt is solvated. In one embodiment, the solvent is toluene.

In certain embodiments, the molar ratio of 4-fluorophenyl)(4-(5-methyl-1H-pyrazol-3-ylamino)quinazolin-2-yl)methanol versus hydrobromic acid in the salt provided herein, including hydrates and pharmaceutically acceptable solvates thereof, is ranging from about 0.5 to about 3, from about 0.5 to about 2, from about 0.8 to about 1.2, from about 0.9 to about 1.1, or from about 0.95 to about 1.05. In certain embodiments, the molar ratio of 4-fluorophenyl)(4-(5-methyl-1H-pyrazol-3-ylamino)quinazolin-2-yl)methanol versus hydrobromic acid in the salt provided herein, including hydrates and pharmaceutically acceptable solvates thereof, is about 0.5, about 0.6, about 0.7, about 0.8, about 0.9, about 0.95, about 1, about 1.05, about 1.1, about 1.2, about 1.4, about 1.5, about 1.6, about 1.8, about 2, about 2.2, about 2.4, about 2.6, about 2.8, or about 3. In certain embodiments, the molar ratio of 4-fluorophenyl)(4-(5-methyl-1H-pyrazol-3-ylamino)quinazolin-2-yl)methanol versus hydrobromic acid in the salt provided herein, including hydrates and pharmaceutically acceptable solvates thereof, is about 1.

In one embodiment, the hydrobromide salt of 4-fluorophenyl)(4-(5-methyl-1H-pyrazol-3-ylamino)quinazolin-2-yl)methanol, or a hydrate or pharmaceutically acceptable solvate thereof, comprises about one molar equivalent of 4-fluorophenyl)(4-(5-methyl-1H-pyrazol-3-ylamino)quinazolin-2-yl)methanol and about one molar equivalent of hydrobromic acid.

In certain embodiments, the hydrobromide salt of 4-fluorophenyl)(4-(5-methyl-1H-pyrazol-3-ylamino)quinazolin-2-yl)methanol, or a hydrate or pharmaceutically acceptable solvate thereof, has a purity of at least about 95%, at least about 96%, at least about 97%, at least about 98%, at least about 98.5%, at least about 99%, at least about 99.2%, at least about 99.4%, at least about 99.5%, at least about 99.6%, at least about 99.7%, at least about 99.8%, or at least about 99.9%. In certain embodiments, the hydrobromide salt of 4-fluorophenyl)(4-(5-methyl-1H-pyrazol-3-ylamino)quinazolin-2-yl)methanol, or a hydrate or pharmaceutically acceptable solvate thereof, has a purity of about 95%-99.9%, about 96%-99.9%, about 97%-99.9%, about 98%-99.9%, about 98.5%-99.9%, about 99%-99.9%, about 99.2%-99.9%, about 99.4%-99.9%, about 99.5%-99.9%, about 99.6%-99.9%, about 99.7%-99.9%, about 99.8%-99.9%, or about 99.9%. In certain embodiments, the hydrobromide salt of 4-fluorophenyl)(4-(5-methyl-1H-pyrazol-3-ylamino)quinazolin-2-yl)methanol, or a hydrate or pharmaceutically acceptable solvate thereof, has a purity of about 95%, about 96%, about 97%, about 98%, about 98.5%, about 99%, about 99.2%, about 99.4%, about 99.5%, about 99.6%, about 99.7%, about 99.8%, or about 99.9%.

In one embodiment, the hydrobromide salt of 4-fluorophenyl)(4-(5-methyl-1H-pyrazol-3-ylamino)quinazolin-2-yl)methanol, or a hydrate or pharmaceutically acceptable solvate thereof, is in an amorphous form. In another embodiment, the hydrobromide salt of 4-fluorophenyl)(4-(5-methyl-1H-pyrazol-3-ylamino)quinazolin-2-yl)methanol, or a hydrate or pharmaceutically acceptable solvate thereof, is in a crystalline form.

A. Form A

In one embodiment, the hydrobromide salt of 4-fluorophenyl)(4-(5-methyl-1H-pyrazol-3-ylamino)quinazolin-2-yl)methanol is in crystalline Form A. In certain embodiments, the hydrobromide salt in Form A has an X-ray powder diffraction pattern substantially as shown in FIG. 1. In certain embodiments, the hydrobromide salt in Form A has one or more characteristic XRP diffraction peaks at two-theta angles selected from approximately 7.5. 10.8, and 14.8°. In certain embodiments, the hydrobromide salt in Form A has characteristic XRP diffraction peaks at two-theta angles of approximately 7.5, 10.8, and 14.8°. In certain embodiments, the hydrobromide salt in Form A has a characteristic XRP diffraction peak at a two-theta angle of approximately 7.5, 9.3, 10.8, 11.3, 13.3, 14.0, 14.6, 14.8, 15.9, 18.1, 22.1, 22.7, 26.4, or 29.3°. In certain embodiments, the hydrobromide salt in Form A has characteristic XRP diffraction peaks at two-theta angles of approximately 7.5, 9.3, 10.8, 11.3, 13.3, 14.0, 14.6, 14.8, 15.9, 18.1, 22.1, 22.7, 26.4, and 29.3°.

In certain embodiments, the hydrobromide salt in Form A has an endotherm with a peak temperature of about 274° C. In certain embodiments, the hydrobromide salt in Form A shows no greater than about 1%, no greater than about 0.9%, no greater than about 0.8%, no greater than about 0.7%, no greater than about 0.6%, no greater than about 0.5%, no greater than about 0.4%, no greater than about 0.3%, no greater than about 0.2%, or no greater than about 0.1% weight loss between about 25° C. to about 114° C. in a thermogravimetric thermogram. In certain embodiments, the hydrobromide salt in Form A shows about 0.4% weight loss between about 25° C. to about 114° C. in a thermogravimetric thermogram. In certain embodiments, the hydrobromide salt in Form A shows no greater than about 1%, no greater than about 0.9%, no greater than about 0.8%, no greater than about 0.7%, no greater than about 0.6%, no greater than about 0.5%, no greater than about 0.4%, no greater than about 0.3%, no greater than about 0.2%, or no greater than about 0.1% weight loss between about 142° C. to about 218° C. in a thermogravimetric thermogram. In certain embodiments, the hydrobromide salt in Form A shows about 0.3% weight loss between about 142° C. to about 218° C. in a thermogravimetric thermogram.

In certain embodiments, the hydrobromide salt in Form A is non-hygroscopic, e.g., exhibits a mass gain of less than about 2% of when subjected to an increase in humidity from about 0% to about 80% relative humidity (RH). In certain embodiments, the hydrobromide salt in Form A exhibits no greater than about 0.6%, no greater than about 0.5%, no greater than about 0.4%, no greater than about 0.3%, no greater than about 0.2%, or no greater than about 0.1% weight loss upon equilibrium at about 5% RH. In certain embodiments, the hydrobromide salt in Form A exhibits about 0.3% weight loss upon equilibrium at about 5% RH. In certain embodiments, the hydrobromide salt in Form A exhibits no greater than about 5%, no greater than about 4%, no greater than about 3%, no greater than about 2%, no greater than about 1%, no greater than about 0.8%, no greater than about 0.6%, no greater than about 0.4%, no greater than about 0.2%, or no greater than about 0.1% weight gain in response to an increase in humidity from about 5% to about 95% relative humidity at 25° C. In certain embodiments, the hydrobromide salt in Form A shows about 1% weight gain in response to an increase in humidity from about 5% to about 95% relative humidity at 25° C. In certain embodiments, the hydrobromide salt in Form A shows no greater than about 5%, no greater than about 4%, no greater than about 3%, no greater than about 2%, no greater than about 1%, no greater than about 0.8%, no greater than about 0.6%, no greater than about 0.4%, no greater than about 0.2%, or no greater than about 0.1% weight loss in response to a decrease in humidity from about 95% to about 5% relative humidity at 25° C. In certain embodiments, the hydrobromide salt in Form A shows about 1% weight loss in response to a decrease in humidity from about 95% to about 5% relative humidity at 25° C.

In certain embodiments, the hydrobromide salt in Form A exhibits desirable characteristics for the synthesis, processing, and/or manufacture of a drug product containing the hydrobromide salt. In certain embodiments, the hydrobromide salt in Form A has an advantageous stability profile, which is an important characteristic for processing and manufacturing of a drug product. In certain embodiments, the hydrobromide salt in Form A is stable upon compression.

In certain embodiments, the hydrobromide salt in Form A is substantially pure. In certain embodiments, the substantially hydrobromide salt in Form A is substantially free of other solid forms, e.g., amorphous, and crystalline Forms B, C, D, E, or F. In certain embodiments, the purity of the substantially hydrobromide salt in Form A is no less than about 95%, no less than about 96%, no less than about 97%, no less than about 98%, no less than about 98.5%, no less than about 99%, no less than about 99.5%, or no less than about 99.8%. In certain embodiments, the purity of the substantially hydrobromide salt in Form A is about 95%-99.8%, about 96%-99.8%, about 97%-99.8%, about 98%-99.8%, about 98.5%-99.8%, about 99%-99.8%, about 99.5%-99.8%, or about 99.8%. In certain embodiments, the purity of the substantially hydrobromide salt in Form A is about 95%, about 96%, about 97%, no less than about 98%, about 98.5%, about 99%, about 99.5%, or about 99.8%.

In one embodiment, the hydrobromide salt in Form A has approximate unit cell dimensions of: a=8.6 Å, b=9.8 Å, c=12.6 Å, α=77°, β=73°, and γ=84°. In another embodiment, the hydrobromide salt in Form A has approximate unit cell dimensions of: a=8.55 Å, b=9.75 Å, c=12.61 Å, α=77.3°, β=72.7°, and γ=84.0°. In yet another embodiment, the hydrobromide salt in Form A has approximate unit cell dimensions of: a=8.554 Å, b=9.753 Å, c=12.610 Å, α=77.32°, β=72.71°, and γ=83.96°. In yet another embodiment, the hydrobromide salt in Form A has a unit cell of a space group of $P_1$. In yet another embodiment, the hydrobromide salt in Form A has a unit cell of a space group of $P_{-1}$. In yet another embodiment, the hydrobromide salt in Form A has a volume of about 979 Å$^3$/cell. In yet another embodiment, the hydrobromide salt in Form A has a V/Z value of about 490 Å$^3$/formula unit. In yet another embodiment, the hydrobromide salt in Form A has a density of about 1.46 g/cm$^3$.

B. Form B

In another embodiment, the hydrobromide salt of 4-fluorophenyl)(4-(5-methyl-1H-pyrazol-3-ylamino)quinazolin-2-yl)methanol is in crystalline Form B. In certain embodiments, the hydrobromide salt in Form B has one or more characteristic XRP diffraction peaks at two-theta angles selected from approximately 4.9, 6.7, and 18.6°. In certain embodiments, the hydrobromide salt in Form B has characteristic XRP diffraction peaks at two-theta angles of approximately 4.9, 6.7, and 18.6°.

C. Form C

In yet another embodiment, the hydrobromide salt of 4-fluorophenyl)(4-(5-methyl-1H-pyrazol-3-ylamino)quinazolin-2-yl)methanol is in crystalline Form C.

Figure 2:
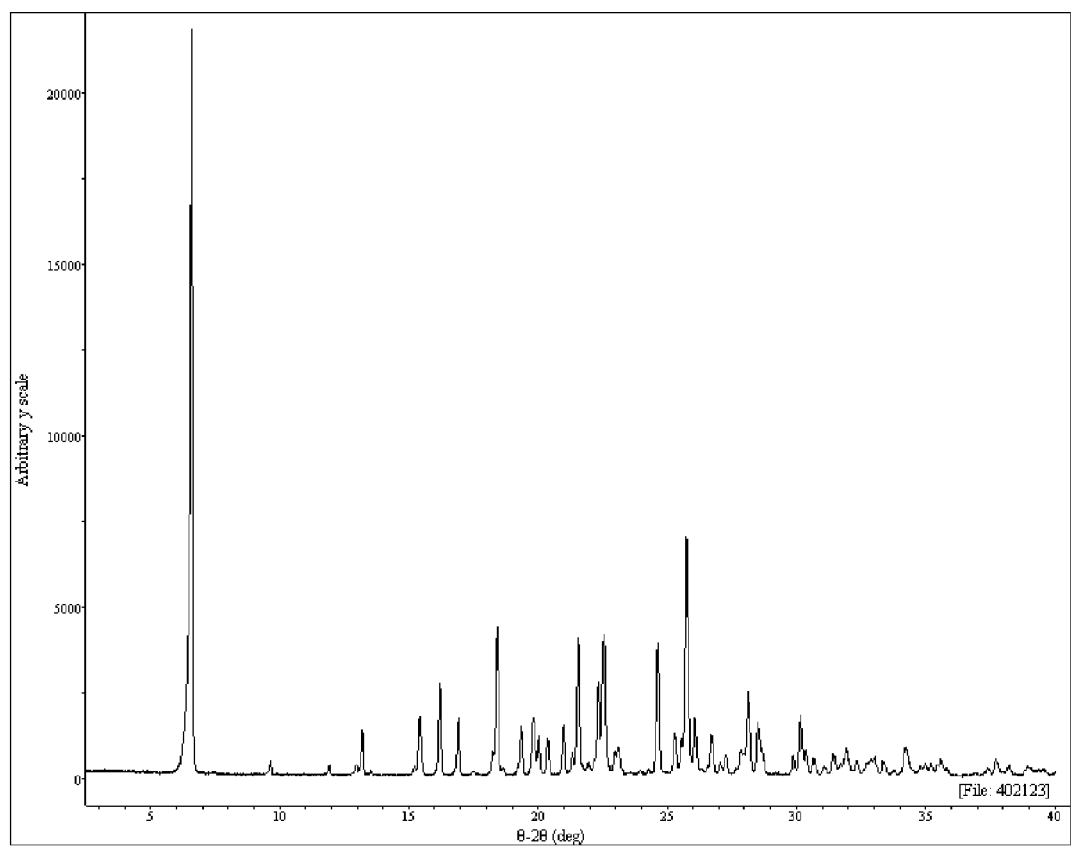
FIG. 2 depicts an X-ray powder (XRP) diffractogram of a hydrobromide salt of (4-fluorophenyl)(4-(5-methyl-1H-pyrazol-3-ylamino)quinazolin-2-yl)methanol in crystalline Form C.

In certain embodiments, the hydrobromide salt in Form C has an X-ray powder diffraction pattern substantially as shown in FIG. 2. In certain embodiments, the hydrobromide salt in Form B has one or more characteristic XRP diffraction peaks at two-theta angles selected from approximately 6.6 and 18.4°. In certain embodiments, the hydrobromide salt in Form B has characteristic XRP diffraction peaks at two-theta angles of approximately 6.6 and 18.4°. In certain embodiments, the hydrobromide salt in Form C has a characteristic XRP diffraction peak at a two-theta angle of approximately 6.6, 11.9, 13.5, 15.2, 15.4, 17.5, 17.7, 18.2, 18.4, 19.3, 19.8, 20.0, 20.3, 22.3, 24.6, 25.5, 27.0, 27.3, or 27.8°. In certain embodiments, the hydrobromide salt in Form C has characteristic XRP diffraction peaks at two-theta angles of approximately 6.6, 11.9, 13.5, 15.2, 15.4, 17.5, 17.7, 18.2, 18.4, 19.3, 19.8, 20.0, 20.3, 22.3, 24.6, 25.5, 27.0, 27.3, and 27.8°.

In certain embodiments, the hydrobromide salt in Form C has an endotherm with a peak temperature of about 222° C. In certain embodiments, the hydrobromide salt in Form C has an endotherm with a peak temperature of about 273° C. In certain embodiments, the hydrobromide salt in Form C shows no greater than about 20%, no greater than about 18%, no greater than about 16%, no greater than about 14%, no greater than about 12%, no greater than about 10%, no greater than about 8%, no greater than about 6%, no greater than about 4%, or no greater than about 2% weight loss between about 132° C. to about 253° C. in a thermogravimetric thermogram. In certain embodiments, the hydrobromide salt in Form C shows about 10% weight loss between about 132° C. to about 253° C. in a thermogravimetric thermogram.

In certain embodiments, the hydrobromide salt in Form C exhibits desirable characteristics for the synthesis, processing, and/or manufacture of a drug product containing the hydrobromide salt. In certain embodiments, the hydrobromide salt in Form C has an advantageous stability profile, which is an important characteristic for processing and manufacturing of a drug product. In certain embodiments, the hydrobromide salt in Form C is stable upon compression.

In certain embodiments, the hydrobromide salt in Form C is substantially pure. In certain embodiments, the substantially hydrobromide salt in Form C is substantially free of other solid forms, e.g., amorphous, and crystalline Forms A, B, D, E, or F. In certain embodiments, the purity of the substantially hydrobromide salt in Form C is no less than about 95%, no less than about 96%, no less than about 97%, no less than about 98%, no less than about 98.5%, no less than about 99%, no less than about 99.5%, or no less than about 99.8%. In certain embodiments, the purity of the substantially hydrobromide salt in Form C is about 95%-99.8%, about 96%-99.8%, about 97%-99.8%, about 98%-99.8%, about 98.5%-99.8%, about 99%-99.8%, about 99.5%-99.8%, or about 99.8%. In certain embodiments, the purity of the substantially hydrobromide salt in Form C is about 95%, about 96%, about 97%, no less than about 98%, about 98.5%, about 99%, about 99.5%, or about 99.8%.

In one embodiment, the hydrobromide salt in Form C has approximate unit cell dimensions of: a=8.6 Å, b=9.8 Å, c=14.1 Å, α=107°, β=92°, and γ=99°. In another embodiment, the hydrobromide salt in Form C has approximate unit cell dimensions of: a=8.60 Å, b=9.77 Å, c=14.12 Å, α=107.4°, β=91.6°, and γ=99.0°. In yet another embodiment, the hydrobromide salt in Form C has approximate unit cell dimensions of: a=8.602 Å, b=9.767 Å, c=14.118 Å, α=107.44°, β=91.55°, and γ=98.96°. In yet another embodiment, the hydrobromide salt in Form C has a unit cell of a space group of $P_1$. In yet another embodiment, the hydrobromide salt in Form C has a unit cell of a space group of $P_{-1}$. In yet another embodiment, the hydrobromide salt in Form C has a volume of about 1114 Å$^3$/cell. In yet another embodiment, the hydrobromide salt in Form C has a V/Z value of about 557 Å$^3$/formula unit. In yet another embodiment, the hydrobromide salt in Form C has a density of about 1.282 g/cm$^3$.

In certain embodiments, the hydrobromide salt in Form C is a solvate of a hydrobromide salt of 4-fluorophenyl)(4-(5-methyl-1H-pyrazol-3-ylamino)quinazolin-2-yl)methanol. In certain embodiments, the hydrobromide salt in Form C contains about 0.4 moles of toluene per mole of 4-fluorophenyl)(4-(5-methyl-1H-pyrazol-3-ylamino)quinazolin-2-yl)methanol. In certain embodiments, the hydrobromide salt in Form C has a peak at about 2.31, 7.18, or 7.25 ppm in a $^1$HNMR spectrum. In certain embodiments, the hydrobromide salt in Form C has peaks at about 2.31, 7.18, and 7.25 ppm in a $^1$HNMR spectrum.

D. Form D

In yet another embodiment, the hydrobromide salt of 4-fluorophenyl)(4-(5-methyl-1H-pyrazol-3-ylamino)quinazolin-2-yl)methanol is in crystalline Form D. In certain embodiments, the hydrobromide salt in Form D has one or more characteristic XRP diffraction peaks at two-theta angles selected from approximately 7.4, 10.8, and 14.8°.

E. Form E

In yet another embodiment, the hydrobromide salt of 4-fluorophenyl)(4-(5-methyl-1H-pyrazol-3-ylamino)quinazolin-2-yl)methanol is in crystalline Form E.

Figure 3:
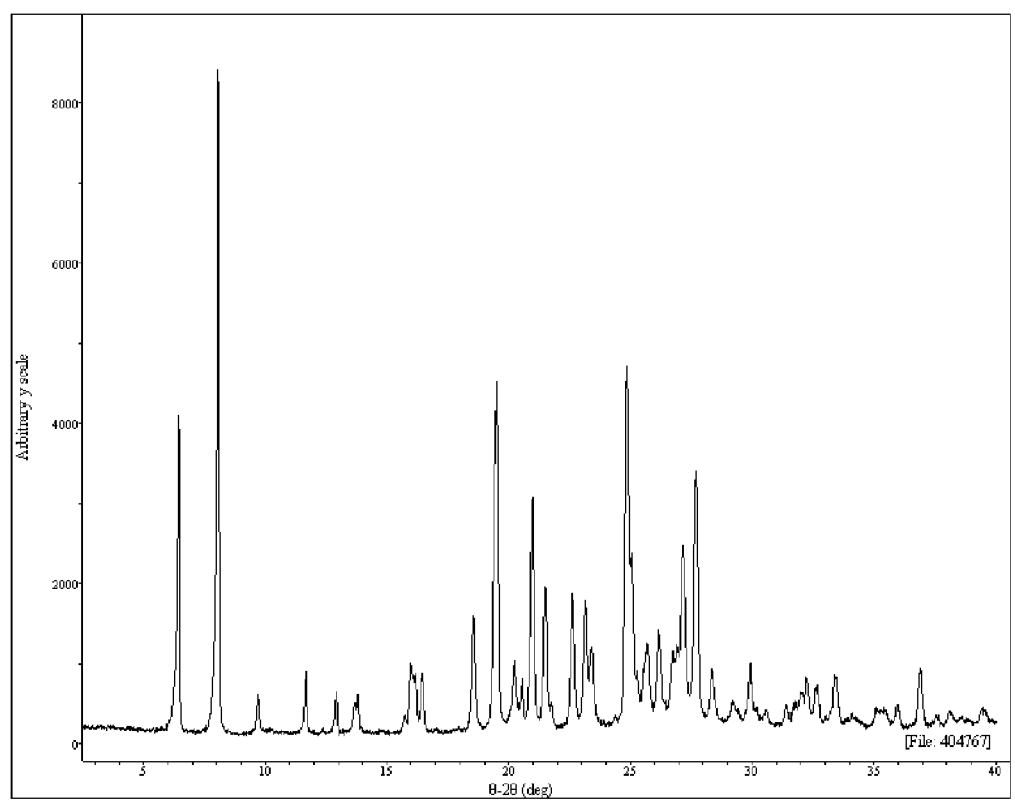
FIG. 3 depicts an X-ray powder (XRP) diffractogram of a hydrobromide salt of (4-fluorophenyl)(4-(5-methyl-1H-pyrazol-3-ylamino)quinazolin-2-yl)methanol in crystalline Form E.

In certain embodiments, the hydrobromide salt in Form E has an X-ray powder diffraction pattern substantially as shown in FIG. 3. In certain embodiments, the hydrobromide salt in Form E has one or more characteristic XRP diffraction peaks at two-theta angles selected from approximately 6.4, 8.0, 11.7, and 19.5°. In certain embodiments, the hydrobromide salt in Form E has characteristic XRP diffraction peaks at two-theta angles of approximately 6.4, 8.0, 11.7, and 19.5°. In certain embodiments, the hydrobromide salt in Form E has a characteristic XRP diffraction peak at a two-theta angle of approximately 6.4, 8.0, 11.7, 13.7, 13.8, 15.7, 16.0, 19.5, 20.5, 21.7, 24.8, 25.0, 25.7, 27.1, 28.3, or 29.2°. In certain embodiments, the hydrobromide salt in Form E has characteristic XRP diffraction peaks at two-theta angles of approximately 6.4, 8.0, 11.7, 13.7, 13.8, 15.7, 16.0, 19.5, 20.5, 21.7, 24.8, 25.0, 25.7, 27.1, 28.3, and 29.2°.

In certain embodiments, the hydrobromide salt in Form E has an endotherm with a peak temperature of about 2, about 76, about 174, or about 201° C. In certain embodiments, the hydrobromide salt in Form E has an exotherm with a peak temperature of about 186° C. In certain embodiments, the hydrobromide salt in Form E shows no greater than about 20%, no greater than about 18%, no greater than about 16%, no greater than about 14%, no greater than about 12%, no greater than about 10%, no greater than about 8%, no greater than about 6%, no greater than about 4%, or no greater than about 2% weight loss between about 26° C. to about 81° C. in a thermogravimetric thermogram. In certain embodiments, the hydrobromide salt in Form E shows about 12% weight loss between about 26° C. to about 81° C. in a thermogravimetric thermogram. In certain embodiments, the hydrobromide salt in Form E shows no greater than about 10%, no greater than about 8%, no greater than about 6%, no greater than about 4%, no greater than about 2%, no greater than about 1%, no greater than about 0.8%, no greater than about 0.6%, no greater than about 0.4%, or no greater than about 0.2% weight loss between about 100° C. to about 182° C. in a thermogravimetric thermogram. In certain embodiments, the hydrobromide salt in Form E shows about 2% weight loss between about 100° C. to about 182° C. in a thermogravimetric thermogram. In certain embodiments, the hydrobromide salt in Form E exhibits desirable characteristics for the synthesis, processing, and/or manufacture of a drug product containing the hydrobromide salt. In certain embodiments, the hydrobromide salt in Form E has an advantageous stability profile, which is an important characteristic for processing and manufacturing of a drug product. In certain embodiments, the hydrobromide salt in Form E is stable upon compression.

In certain embodiments, the hydrobromide salt in Form E is non-hygroscopic, e.g., exhibits a mass gain of less than about 2% of when subjected to an increase in humidity from about 0% to about 80% relative humidity (RH). In certain embodiments, the hydrobromide salt in Form E exhibits no greater than about 1%, no greater than about 0.8%, no greater than about 0.6%, no greater than about 0.4%, no greater than about 0.2%, or no greater than about 0.1% weight gain in response to an increase in humidity from about 5% to about 95% relative humidity at 25° C. In certain embodiments, the hydrobromide salt in Form E shows about 0.6% weight gain in response to an increase in humidity from about 5% to about 95% relative humidity at 25° C. In certain embodiments, the hydrobromide salt in Form E shows no greater than about 1%, no greater than about 0.8%, no greater than about 0.6%, no greater than about 0.4%, no greater than about 0.2%, or no greater than about 0.1% weight loss in response to a decrease in humidity from about 95% to about 5% relative humidity at 25° C. In certain embodiments, the hydrobromide salt in Form E shows about 0.6% weight loss in response to a decrease in humidity from about 95% to about 5% relative humidity at 25° C.

In certain embodiments, the hydrobromide salt in Form E is substantially pure. In certain embodiments, the substantially hydrobromide salt in Form E is substantially free of other solid forms, e.g., amorphous, and crystalline Forms A, B, C, D, or F. In certain embodiments, the purity of the substantially hydrobromide salt in Form E is no less than about 95%, no less than about 96%, no less than about 97%, no less than about 98%, no less than about 98.5%, no less than about 99%, no less than about 99.5%, or no less than about 99.8%. In certain embodiments, the purity of the substantially hydrobromide salt in Form E is about 95%-99.8%, about 96%-99.8%, about 97%-99.8%, about 98%-99.8%, about 98.5%-99.8%, about 99%-99.8%, about 99.5%-99.8%, or about 99.8%. In certain embodiments, the purity of the substantially hydrobromide salt in Form E is about 95%, about 96%, about 97%, no less than about 98%, about 98.5%, about 99%, about 99.5%, or about 99.8%.

In one embodiment, the hydrobromide salt in Form E has approximate unit cell dimensions of: a=7.2 Å, b=18.2 Å, c=27.4 Å, α=90°, β=90°, and γ=90°. In another embodiment, the hydrobromide salt in Form E has approximate unit cell dimensions of: a=7.17 Å, b=18.22 Å, c=27.45 Å, α=90°, β=90°, and γ=90°. In yet another embodiment, the hydrobromide salt in Form E has approximate unit cell dimensions of: a=7.166 Å, b=18.223 Å, c=27.449 Å, α=90°, β=90°, and γ=90°. In yet another embodiment, the hydrobromide salt in Form E has a volume of about 3585 Å$^3$/cell. In yet another embodiment, the hydrobromide salt in Form E has a V/Z value of about 448 Å$^3$/asym. unit. In yet another embodiment, the hydrobromide salt in Form E has a density of about 1.59 g/cm$^3$.

F. Form F

In still another embodiment, the hydrobromide salt of 4-fluorophenyl)(4-(5-methyl-1H-pyrazol-3-ylamino) quinazolin-2-yl)methanol is in crystalline Form F. In certain embodiments, the hydrobromide salt in Form F has a characteristic XRP diffraction peak at a two-theta angle of approximately 6.6°.

The purity of the salts provided herein may be determined by standard analytical methods, such as thin layer chromatography (TLC), gel electrophoresis, gas chromatography, high performance liquid chromatography (HPLC), and mass spectrometry (MS). The salts provided herein in solid forms may be characterized using a number of methods known to a person skilled in the art, including, but not limited to, single crystal X-ray diffraction, X-ray powder diffraction (XRPD), microscopy (e.g., scanning electron microscopy (SEM)), thermal analysis (e.g., differential scanning calorimetry (DSC), thermal gravimetric analysis (TGA), and hot-stage microscopy), and spectroscopy (e.g., infrared, Raman, and solid-state nuclear magnetic resonance). The particle size and size distribution of the salts provided herein in solid forms may be determined by conventional methods, such as laser light scattering technique.

It should be understood that the numerical values of the peaks of the X-ray powder diffraction patterns may vary slightly from one machine to another or from one sample to another, and so the values quoted are not to be construed as absolute, but with an allowable variability, such as 0.1°, which is recommended in the United State Pharmacopeia (pages: 387-389, 2007).

Process of Preparation

In one embodiment, provided herein is a process for preparing a hydrobromide salt of 4-fluorophenyl)(4-(5-methyl-1H-pyrazol-3-ylamino)quinazolin-2-yl)methanol as provided herein, or a hydrate or pharmaceutically acceptable solvate thereof; which comprises reacting 4-fluorophenyl)(4-(5-methyl-1H-pyrazol-3-ylamino)quinazolin-2-yl)methanol with hydrobromic acid in a solvent at a first predetermined temperature. In another embodiment, the process further comprises precipitating the salt at a second predetermined temperature.

Suitable solvents for use in preparing the salt provided herein include, but are not limited to, hydrocarbons, including petroleum ether, pentane, hexane(s), heptane(s), octane, isooctane, cyclopentane, cyclohexane, methylcyclohexane, benzene, toluene, xylene, tetralin, and cumene; halogenated hydrocarbons, including dichloromethane (DCM), 1,2-dichloroethane, 1,1-dichloroethene, 1,2-dichloroethene, chloroform, trichloroethane, trichloroethene, carbon tetrachloride, tetrafluoroethene, methylcyclohexane, chlorobenzene, and trifluoromethylbenzene; alcohols, including methanol (MeOH), ethanol (EtOH), trifluoroethanol (TFE), isopropanol (IPA), 1-propanol, hexafluoroisopropanol, 1-butanol, 2-butanol, t-butanol, 2-methyl-1-propanol, 3-methyl-1-butanol, 1-pentanol, tent-amyl alcohol, 2-methoxyethanol, 2-ethoxyethanol, and ethyleneglycol; ethers, including diethyl ether, diisopropyl ether, methyl t-butyl ether (MTBE), methyl nonafluorobutyl ether, diphenyl ether, 1,2-dimethoxyethane, bi(2-methoxyethyl)ether, 1,1-dimethoxymethane, 2,2-dimethoxypropane, and anisole; ketones, including acetone, butanone, methyl ethyl ketone (MEK), methyl isopropyl ketone, methyl butyl ketone, methyl isobutyl ketone (MIBK), 3-pentanone, and cyclopentanone; esters, including methyl acetate, ethyl formate, ethyl acetate (EtOAc), ethyl trifluoroacetate, propyl acetate, isopropyl acetate (IPAc), isobutyl acetate, and butyl acetate; carbonates, including ethylene carbonate and propylene carbonate; amides, including formamide, N,N-dimethylformamide (DMF), and N,N-dimethylacetamide; nitriles, including acetonitrile (ACN) and propionitrile; sulfoxides, including dimethyl sulfoxide (DMSO); sulfones, including sulfolane; nitro compounds, including nitromethane and nitrobenzene; heterocycles, including N-methyl pyrrolindone, 2-methyl tetrahydrofuran, tetrahydrofuran (THF), dioxane, and pyridine; carboxylic acids, including acetic acid, trichloroacetic acid, and trifluoroacetic acid; phosphoramides, including hexamethylphosphoramide; carbon sulfide; water; and mixtures thereof.

In certain embodiments, the solvent is acetone, acetonitrile, tert-butanol, chloroform, N,N-dimethylformamide, dimethyl sulfoxide, ethanol, ethyl acetate, heptane, hexafluoroisopropanol, isopropanol, isopropyl ether, methanol, methyl ethyl ketone, nitromethane, tetrahydrofuran, toluene, trifluoroethanol, water, or a mixture thereof.

In certain embodiments, the salt forming step is carried out at a temperature from about −10 to about 150° C., from about 10 to about 110° C., or from about 20 to about 100° C. In certain embodiments, the salt forming reaction is carried out at a temperature of about 20° C., about 25° C., about 30° C., about 35° C., about 40° C., about 45° C., or about 50° C.

In certain embodiments, the salt forming step is performed in the presence of about one equivalent of an acid. In certain embodiments, the salt forming step is performed in the presence of an excess amount of an acid to maximize the yield of the reaction. In certain embodiments, the molar ratio of the acidic group on the acid versus the compound of Formula I is about 1, about 1.01, about 1.05, about 1.1, or about 1.2. In certain embodiments, the molar ratio of the acidic group on the acid versus the compound of Formula I is ranging from about 0.5 to about 10, from about 0.9 to about 5, or from about 0.95 to about 2.5.

In certain embodiments, the salt forming step is performed in a solution, that is, both the compound of Formula I and the acid are dissolved in the solvent. In certain embodiments, the salt forming step is performed as a slurry mixture of the compound of Formula I and the acid in the solvent. In certain embodiments, the compound of Formula I is not fully dissolved, whereas the acid is completely dissolved.

In certain embodiments, the salt provided herein is precipitated out from the reaction solution or slurry mixture using conventional methods, including, but not limited to, cooling, chilling, solvent evaporation, addition of an anti-solvent, or reverse addition of the mixture of the salt into an anti-solvent. In certain embodiments, the salt provided herein is precipitated out from the reaction solution or slurry mixture upon cooling.

In certain embodiments, the salt provided herein is precipitated out from the reaction solution or slurry mixture via the addition of an anti-solvent. Suitable anti-solvents include, but are not limited to, hydrocarbons, including petroleum ether, pentane, hexane(s), heptane(s), octane, isooctane, cyclopentane, cyclohexane, methylcyclohexane, benzene, toluene, xylene, tetralin, and cumene; halogenated hydrocarbons, including 1,2-dichloroethane, 1,1-dichloroethene, 1,2-dichloroethene, chloroform, trichloroethane, trichloroethene, carbon tetrachloride, tetrafluoroethene, chlorobenzene, and trifluoromethylbenzene; alcohols, including 1-butanol, 2-butanol, t-butanol, 2-methyl-1-propanol, 3-methyl-1-butanol, 1-pentanol, tert-amyl alcohol, 2-methoxyethanol, 2-ethoxyethanol, and ethyleneglycol; ethers, including diethyl ether, diisopropyl ether, methyl t-butyl ether (MTBE), methyl nonafluorobutyl ether, diphenyl ether, 1,2-dimethoxyethane, bi(2-methoxyethyl)ether, 1,1-dimethoxymethane, 2,2-dimethoxypropane, and anisole; ketones, including butanone, methyl ethyl ketone (MEK), methyl isopropyl ketone, methyl butyl ketone, methyl isobutyl ketone (MIBK), 3-pentanone, and cyclopentanone; esters, including isobutyl acetate, and butyl acetate; carbonates, including ethylene carbonate and propylene carbonate; sulfones, including sulfolane; nitro compounds, including nitromethane and nitrobenzene; heterocycles, including dioxane and pyridine; carbon sulfide; water; and mixtures thereof. In certain embodiments, the anti-solvent is acetonitrile, chloroform, ethanol, ethyl acetate, heptane, isopropanol, isopropyl ether, methyl ethyl ketone, nitromethane, toluene, water, tetrahydrofuran, or a mixture thereof.

When two solvents are used as a solvent/anti-solvent pair, the salt provided herein has a higher solubility in the solvent than in the anti-solvent. In certain embodiments, the solvent and the anti-solvent in a solvent/anti-solvent pair are at least partially miscible.

In certain embodiments, the precipitating step is carried out at a temperature from about −50 to about 100° C., from about −30 to about 50° C., or from about −10 to about 30° C. In certain embodiments, the precipitating step is carried out at a temperature of about 0° C., about 5° C., about 10° C., about 15° C., about 20° C., about 25° C., or about 30° C.

To accelerate the precipitation (crystallization) step, the process may further comprise the step of seeding the reaction solution or mixture, prior to or during the initiation of the precipitation step. The amount of seed crystals added exceeds the saturation amount in the solvent being used so that there are undissolved seed crystals present in the reaction solution.

In certain embodiments, the process further comprises an isolation step, in which the precipitate is isolated by a conventional method, such as filtration and centrifugation, followed by washing with a solvent and then drying.

Other salt forming methods may also be applicable in the present disclosure. For example, the salt of the compound of Formula I may be prepared by converting a salt of the compound, e.g., an HCl salt, to a hydrobromide salt via anion exchange using an anion exchange column.

In addition to precipitation and crystallization, the solid salt provided herein may also be prepared using conventional methods known to those skilled in the art, including spray drying, roller drying, lyophilization, and melt crystallization.

Pharmaceutical Compositions

In one embodiment, provided herein are pharmaceutical compositions comprising a hydrobromide salt of (4-fluorophenyl)(4-(5-methyl-1H-pyrazol-3-ylamino)quinazolin-2-yl)methanol, or a hydrate or pharmaceutically acceptable solvate thereof, or a crystalline form thereof, including Forms A, B, C, D, E, and F; and a pharmaceutically acceptable vehicle, carrier, diluent, or excipient, or a mixture thereof.

In certain embodiment, the hydrobromide salt is in a crystalline form. In one embodiment, the hydrobromide salt as used in the pharmaceutical composition provided herein is in crystalline Form A. In another embodiment, the hydrobromide salt as used in the pharmaceutical composition provided herein is in crystalline Form B. In yet another embodiment, the hydrobromide salt as used in the pharmaceutical composition provided herein is in crystalline Form C. In yet another embodiment, the hydrobromide salt as used in the pharmaceutical composition provided herein is in crystalline Form D. In yet another embodiment, the hydrobromide salt as used in the pharmaceutical composition provided herein is in crystalline Form E. In still another embodiment, the hydrobromide salt as used in the pharmaceutical composition provided herein is in crystalline Form F.

Suitable excipients are well known to those skilled in the art, and non-limiting examples of suitable excipients are provided herein. Whether a particular excipient is suitable for incorporation into a pharmaceutical composition or dosage form depends on a variety of factors well known in the art, including, but not limited to, the method of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided herein are pharmaceutical compositions and dosage forms that contain little, if any, lactose, or other mono- or di-saccharides. As used herein, the term "lactose-free" means that the amount of lactose present, if any, is insufficient to substantially increase the degradation rate of an active ingredient. In one embodiment, lactose-free compositions comprise an active ingredient provided herein, a binder/filler, and a lubricant. In another embodiment, lactose-free dosage forms comprise an active ingredient, microcrystalline cellulose, pre-gelatinized starch, and magnesium stearate.

The hydrobromide salt provided herein may be administered alone, or in combination with one or more other salts provided herein. The pharmaceutical compositions that comprise a salt provided herein can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd ed.; Rathbone et al., Eds.; Marcel Dekker, Inc.: New York, N.Y., 2008).

In one embodiment, the pharmaceutical compositions are provided in a dosage form for oral administration, which comprise a salt provided herein, and one or more pharmaceutically acceptable vehicles, carriers, diluents, or excipients.

In another embodiment, the pharmaceutical compositions are provided in a dosage form for parenteral administration, which comprise a salt provided herein, and one or more pharmaceutically acceptable vehicles, carriers, diluents, or excipients.

In yet another embodiment, the pharmaceutical compositions are provided in a dosage form for topical administration, which comprise a salt provided herein, and one or more pharmaceutically acceptable vehicles, carriers, diluents, or excipients.

The pharmaceutical compositions provided herein can be provided in a unit-dosage form or multiple-dosage form. A unit-dosage form, as used herein, refers to a physically discrete unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. For example, a 100 mg unit dose contains about 100 mg of an active ingredient in a packaged tablet or capsule. A unit-dosage form may be administered in fractions or multiples thereof. A multiple-dosage form is a plurality of identical unit-dosage forms packaged in a single container to be administered in segregated unit-dosage forms. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W. R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve a plurality of functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, pulmonary, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, Remington: The Science and Practice of Pharmacy, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphorism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,958,458; 5,972,891; 5,980,945; 5,993,855; 6,045,830; 6,087,324; 6,113,943; 6,197,350; 6,248,363; 6,264,970; 6,267,981; 6,270,798; 6,375,987; 6,376,461; 6,419,961; 6,589,548; 6,613,358; 6,623,756; 6,699,500; 6,793,936; 6,827,947; 6,902,742; 6,958,161; 7,255,876; 7,416,738; 7,427,414; 7,485,322; Bussemer et al., *Crit. Rev. Ther. Drug Carrier Syst.* 2001, 18, 433-458; *Modified-Release Drug Delivery Technology*, 2nd ed.; Rathbone et al., Eds.; Marcel Dekker AG: 2005; Maroni et al., *Expert. Opin. Drug Deliv.* 2005, 2, 855-871; Shi et al., *Expert Opin. Drug Deliv.* 2005, 2, 1039-1058; *Polymers in Drug Delivery*; Ijeoma et al., Eds.; CRC Press LLC: Boca Raton, Fla., 2006; Badawy et al., *J. Pharm. Sci.* 2007, 9, 948-959; *Modified-Release Drug Delivery Technology*, supra; Conway, *Recent Pat. Drug Deliv. Formul.* 2008, 2, 1-8; Gazzaniga et al., *Eur. J. Pharm. Biopharm.* 2008, 68, 11-18; Nagarwal et al., *Curr. Drug Deliv.* 2008, 5, 282-289; Gallardo et al., *Pharm. Dev. Technol.* 2008, 13, 413-423; Chrzanowski, *AAPS PharmSciTech.* 2008, 9, 635-638; Chrzanowski, *AAPS PharmSciTech.* 2008, 9, 639-645; Kalantzi et al., *Recent Pat. Drug Deliv. Formul.* 2009, 3, 49-63; Saigal et al., *Recent Pat. Drug Deliv. Formul.* 2009, 3, 64-70; and Roy et al., *J. Control Release* 2009, 134, 74-80.

1. Matrix Controlled Release Devices

The pharmaceutical compositions provided herein in a modified release dosage form can be fabricated using a matrix controlled release device known to those skilled in the art. See, Takada et al. in *Encyclopedia of Controlled Drug Delivery*; Mathiowitz Ed.; Wiley: 1999; Vol. 2.

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(–)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art. See, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; and Verma et al., *J. Controlled Release* 2002, 79, 7-27.

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and International Pat. Appl. Publ. No. WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxyethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet-and dry-granulation, extrusion/spheronization, roller-compaction, melt-congealing, and by spray-coating seed cores. See, for example, *Multiparticulate Oral Drug Delivery*; Ghebre-Sellassie Ed.; Marcel Dekker: 1994; and *Pharmaceutical Pelletization Technology*; Ghebre-Sellassie Ed.; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 5,709,874; 5,759,542; 5,840,674; 5,900,252; 5,972,366; 5,985,307; 6,004,534; 6,039,975; 6,048,736; 6,060,082; 6,071,495; 6,120,751; 6,131,570; 6,139,865; 6,253,872; 6,271,359; 6,274,552; 6,316,652; and 7,169,410.

Methods of Use

In one embodiment, provided herein is a method of treating a proliferative disease in a subject, comprising administering to the subject a therapeutically effective amount of a hydrobromide salt of (4-fluorophenyl)(4-(5-methyl-1H-pyrazol-3-ylamino)quinazolin-2-yl)methanol, or a hydrate or pharmaceutically acceptable solvate thereof, or a crystalline form thereof, including Forms A, B, C, D, E, and F.

In certain embodiments, the proliferative disease is a myeloproliferative disorder, including, but not limited to, polycythemia vera (PCV), essential thrombocythemia, and idiopathic myelofibrosis (IMF). In certain embodiments, the proliferative disease is leukemia, including, but not limited to, myeloid leukemia, chronic myeloid leukemia (CML), imatinib-resistant CMLs, acute myeloid leukemia (AML), and acute megakaryoblastic leukemia (AMKL). In certain embodiments, the proliferative disease is a lymphoproliferative disease, including, but not limited to, myeloma. In certain embodiments, the proliferative disease is cancer, including, but not limited to, head and neck cancer, prostate cancer, breast cancer, ovarian cancer, melanoma, lung cancer, brain tumor, pancreatic cancer, and renal carcinoma. In certain embodiments, the proliferative disease is a inflammatory disease or disorder, including, but not limited to, immune dysfunction, immunodeficiency, immunomodulation, autoimmune diseases, tissue transplant rejection, graft-versus-host disease, wound healing, kidney disease, multiple sclerosis, thyroiditis, type 1 diabetes, sarcoidosis, psoriasis, allergic rhinitis, inflammatory bowel diseases, Crohn's disease, ulcerative colitis (UC), systemic lupus erythematosis (SLE), arthritis, osteoarthritis, rheumatoid arthritis, osteoporosis, asthma and chronic obstructive pulmonary disease (COPD), and dry eye syndrome (or keratoconjunctivitis sicca (KCS)).

In another embodiment, provided herein is a method of treating, preventing, or ameliorating a JAK-mediated condition, disorder, or disease, in a subject, comprising administering to the subject a therapeutically effective amount of a hydrobromide salt of (4-fluorophenyl)(4-(5-methyl-1H-pyrazol-3-ylamino)quinazolin-2-yl)methanol, or a hydrate or pharmaceutically acceptable solvate thereof, or a crystalline form thereof, including Forms A, B, C, D, E, and F.

In certain embodiments, the JAK-mediated condition, disorder, or disease is a myeloproliferative disorder, including, but not limited to, polycythemia vera (PCV), essential thrombocythemia, and idiopathic myelofibrosis (IMF). In certain embodiments, the JAK-mediated condition, disorder, or disease is leukemia, including, but not limited to, myeloid leukemia, chronic myeloid leukemia (CML), imatinib-resistant CMLs, acute myeloid leukemia (AML), and acute megakaryoblastic leukemia (AMKL). In certain embodiments, the JAK-mediated condition, disorder, or disease is a lymphoproliferative disease, including, but not limited to, myeloma. In certain embodiments, the JAK-mediated condition, disorder, or disease is cancer, including, but not limited to, head and neck cancer, prostate cancer, breast cancer, ovarian cancer, melanoma, lung cancer, brain tumor, pancreatic cancer, and renal carcinoma. In certain embodiments, the JAK-mediated condition, disorder, or disease is a inflammatory disease or disorder, including, but not limited to, immune dysfunction, immunodeficiency, immunomodulation, autoimmune diseases, tissue transplant rejection, graft-versus-host disease, wound healing, kidney disease, multiple sclerosis, thyroiditis, type 1 diabetes, sarcoidosis, psoriasis, allergic rhinitis, inflammatory bowel diseases, Crohn's disease, ulcerative colitis (UC), systemic lupus erythematosis (SLE), arthritis, osteoarthritis, rheumatoid arthritis, osteoporosis, asthma and chronic obstructive pulmonary disease (COPD), and dry eye syndrome (or keratoconjunctivitis sicca (KCS)).

In certain embodiments, provided herein are methods of using the disclosed compounds and compositions, or pharmaceutically acceptable salts, solvates or hydrates thereof, for the treatment, prevention, or amelioration of a disease or disorder selected from myeloproliferative disorders, including, but not limited to, polycythemia vera (PCV), essential thrombocythemia, idiopathic myelofibrosis (IMF), and hypereosinophilic syndrome (HES); leukemia, including, but not limited to, myeloid leukemia, chronic myeloid leukemia (CML), imatinib-resistant CMLs, acute myeloid leukemia (AML), acute lymphoblastic leukemia (ALL), and acute megakaryoblastic leukemia (AMKL); lymphoproliferative diseases, including, but not limited to, myeloma; cancer, including, but not limited to, head and neck cancer, prostate cancer, breast cancer, ovarian cancer, melanoma, lung cancer, brain cancer, pancreatic cancer, gastric cancer, thyroid cancer, renal carcinoma, Kaposi's sarcoma, Castleman's disease, and melanoma; inflammatory diseases or disorders, including, but not limited to immune dysfunction, immunodeficiency or immunomodulation, such as tissue transplant rejection, graft-versus-host disease, wound healing, kidney diseases, autoimmune diseases, multiple sclerosis, thyroiditis, type 1 diabetes, sarcoidosis, psoriasis, allergic rhinitis, atopic dermatitis, myasthenia gravis, inflammatory bowel diseases, Crohn's disease, ulcerative colitis (UC), systemic lupus erythematosis (SLE), arthritis, osteoarthritis, rheumatoid arthritis, osteoporosis, asthma and chronic obstructive pulmonary disease (COPD), conjunctivitis, uveitis, iritis, scleritis, rhinitis, sinusitis, bronchitis, myocarditis, ischemia reperfusion injuries, systemic inflammatory response syndrome (SIRS), and sepsis.

In certain embodiments, JAK-mediated diseases and disorders include, but are not limited to, restenosis, fibrosis, and scleroderma. In certain embodiments, JAK-mediated diseases include, but are not limited to, viral diseases such as Epstein Barr virus (EBV), hepatitis (hepatitis B or hepatitis C), human immunodeficiency virus (HIV), human T-lymphotropic virus type 1 (HTLV-1), varicella-zoster virus, and the human papilloma virus (HPV).

In certain embodiments, the salt provided herein is administered to the subject in the amount ranging from about 0.01 to about 1,000 mg/kg, from about 0.1 to about 500 mg/kg, from about 0.1 to about 250 mg/kg, or from about 0.1 to about 100 mg/kg.

In certain embodiments, the salt provided herein is administered to the subject in the amount ranging from about 0.01 to about 1,000 mg/kg/day, from about 0.1 to about 500 mg/kg/day, from about 0.1 to about 250 mg/kg/day, or from about 0.1 to about 100 mg/kg/day. In certain embodiments, the salt provided herein is administered to the subject in the amount of about 1, about 2, about 3, about 4, about 5, about 6, about 7, about 8, about 9, about 10, about 15, about 20, about 25, about 30, about 35, about 40 about 50, about 60, about 70, about 75, about 80, about 90, about 100, about 105, about 120, about 130, about 140, about 150, about 160, about 170, about 180, about 190, about 200, about 300, about 400, about 500, about 600, about 700, about 750, about 800, about 900, or about 1,000 mg/kg/day.

The administered dose of the salt provided herein can also be expressed in units other than the unit "mg/kg/day." For example, doses for parenteral administration can be expressed as mg/m$^2$/day. One of ordinary skill in the art would readily know how to convert doses from mg/kg/day to mg/m$^2$/day to given either the height or weight of a subject or both (See, www.fda.gov/cder/cancer/animalframe.htm). For example, a dose of 1 mg/kg/day for a 65 kg human is approximately equal to 38 mg/m$^2$/day.

Depending on the disease to be treated and the subject's condition, the salt provided herein can be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The salt provided herein may be formulated, alone or together, in suitable dosage unit with pharmaceutically acceptable excipients, carriers, adjuvants and vehicles, appropriate for each route of administration.

The salt provided herein can be delivered as a single dose such as, e.g., a single bolus injection, or oral tablets or pills; or over time such as, e.g., continuous infusion over time or divided bolus doses over time.

The salt provided herein can be administered once daily (QD), or divided into multiple daily doses such as twice daily (BID), three times daily (TID), and four times daily (QID). In addition, the administration can be continuous, i.e., every day, or intermittently. The term "intermittent" or "intermittently" as used herein is intended to mean stopping and starting at either regular or irregular intervals. For example, intermittent administration of the salt provided herein is administration for one to six days per week, administration in cycles (e.g., daily administration for two to eight consecutive weeks, then a rest period with no administration for up to one week), or administration on alternate days.

In certain embodiments, the frequency of administration of the salt provided herein is in the range of about a daily dose to about a monthly dose. In certain embodiments, the administration of the salt provided herein is once a day, twice a day, three times a day, four times a day, once every other day, twice a week, once every week, once every two weeks, once every three weeks, or once every four weeks. In one embodiment, the salt provided herein is administered once a day. In another embodiment, the salt provided herein is administered twice a day. In yet another embodiment, the salt provided herein is administered three times a day. In still another embodiment, the salt provided herein is administered four times a day.

In certain embodiments, the subject is a mammal. In certain embodiments, the mammal is a human.

In one embodiment, the proliferative disease is a tumor. In another embodiment, the proliferative disease is a solid tumor. In certain embodiments, the solid tumor is an advanced solid tumor. In certain embodiments, the solid tumor is a metastatic solid tumor. In yet another embodiment, the proliferative disease is cancer. In yet another embodiment, the proliferative disease is advanced cancer. In certain embodiments, the solid tumor is metastatic cancer.

In certain embodiments, the cancer treatable with the methods provided herein includes, but is not limited to, (1) leukemias, including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML), (2) chronic leukemias, including, but not limited to, chronic myelocytic (granulocytic) leukemia, chronic lymphocytic leukemia, and hairy cell leukemia; (3) polycythemia vera; (4) lymphomas, including, but not limited to, Hodgkin's disease and non-Hodgkin's disease; (5) multiple myelomas, including, but not limited to, smoldering multiple myeloma, non-secretory myeloma, osteosclerotic myeloma, plasma cell leukemia, solitary plasmacytoma, and extramedullary plasmacytoma; (6) Waldenstrom's macroglobulinemia; (7) monoclonal gammopathy of undetermined significance; (8) benign monoclonal gammopathy; (9) heavy chain disease; (10) bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma; (11) brain tumors, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; (12) breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; (13) adrenal cancer, including, but not limited to, pheochromocytom and adrenocortical carcinoma; (14) thyroid cancer, including, but not limited to, papillary or follicular thyroid cancer, medullary thyroid cancer, and anaplastic thyroid cancer; (15) pancreatic cancer, including, but not limited to, insulinoma, gastrinoma, glucagonoma, vipoma, somatostatin-secreting tumor, and carcinoid or islet cell tumor; (16) pituitary cancer, including, but limited to, Cushing's disease, prolactin-secreting tumor, acromegaly, and diabetes insipius; (17) eye cancer, including, but not limited, to ocular melanoma such as iris melanoma, choroidal melanoma, and cilliary body melanoma, and retinoblastoma; (18) vaginal cancer, including, but not limited to, squamous cell carcinoma, adenocarcinoma, and melanoma; (19) vulvar cancer, including, but not limited to, squamous cell carcinoma, melanoma, adenocarcinoma, basal cell carcinoma, sarcoma, and Paget's disease; (20) cervical cancers, including, but not limited to, squamous cell carcinoma, and adenocarcinoma; (21) uterine cancer, including, but not limited to, endometrial carcinoma and uterine sarcoma; (22) ovarian cancer, including, but not limited to, ovarian epithelial carcinoma, borderline tumor, germ cell tumor, and stromal tumor; (23) esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; (24) stomach cancer, including, but not limited to, adenocarcinoma, fungating (polypoid), ulcerating, superficial spreading, diffusely spreading, malignant lymphoma, liposarcoma, fibrosarcoma, and carcinosarcoma; (25) colon cancer; (26) rectal cancer; (27) liver cancer, including, but not limited to, hepatocellular carcinoma and hepatoblastoma; (28) gallbladder cancer, including, but not limited to, adenocarcinoma; (29) cholangiocarcinomas, including, but not limited to, pappillary, nodular, and diffuse; (30) lung cancer, including, but not limited to, non-small cell lung cancer, squamous cell carcinoma (epidermoid carcinoma), adenocarcinoma, large-cell carcinoma, and small-cell lung cancer; (31) testicular cancer, including, but not limited to, germinal tumor, seminoma, anaplastic, classic (typical), spermatocytic, nonseminoma, embryonal carcinoma, teratoma carcinoma, and choriocarcinoma (yolk-sac tumor); (32) prostate cancer, including, but not limited to, adenocarcinoma, leiomyosarcoma, and rhabdomyosarcoma; (33) penal cancer; (34) oral cancer, including, but not limited to, squamous cell carcinoma; (35) basal cancer; (36) salivary gland cancer, including, but not limited to, adenocarcinoma, mucoepidermoid carcinoma, and adenoidcystic carcinoma; (37) pharynx cancer, including, but not limited to, squamous cell cancer and verrucous; (38) skin cancer, including, but not limited to, basal cell carcinoma, squamous cell carcinoma and melanoma, superficial spreading melanoma, nodular melanoma, lentigo malignant melanoma, and acral lentiginous melanoma; (39) kidney cancer, including, but not limited to, renal cell cancer, adenocarcinoma, hypernephroma, fibrosarcoma, and transitional cell cancer (renal pelvis and/or uterer); (40) Wilms' tumor; (41) bladder cancer, including, but not limited to, transitional cell carcinoma, squamous cell cancer, adenocarcinoma, and carcinosarcoma; and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas (See Fishman et al., 1985, *Medicine*, 2d Ed., J. B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

In certain embodiments, the cancer that is treatable with the methods provided herein includes, but is not limited to, bladder cancer, breast cancer, cervical cancer, colon cancer (e.g., colorectal cancer), endometrial cancer, esophageal cancer, gastric cancer, glioma (e.g., glioblastoma), head and neck cancer, liver cancer, lung cancer (e.g., small cell and non-small cell lung cancers), melanoma, myeloma, neuroblastoma, ovarian cancer, pancreatic cancer, prostate cancer, renal cancer, sarcoma (e.g., osteosarcoma), skin cancer (e.g., squamous cell carcinoma), stomach cancer, testicular cancer, thyroid cancer, and uterine cancer.

In certain embodiments, the cancer that is treatable with the methods provided herein includes, but is not limited to, bladder cancer, breast cancer, cervical cancer, colon cancer (e.g., colorectal cancer), endometrial cancer, gastric cancer, glioma (e.g., glioblastoma), head and neck cancer, liver cancer, non-small cell lung cancer, ovarian cancer, pancreatic cancer, and prostate cancer.

In certain embodiments, the cancer is head and neck cancer. In certain embodiments, the cancer is lung cancer. In certain embodiments, the cancer is lung adenocarcinoma. In certain embodiments, the cancer is esophogeal or upper GI cancer.

In certain embodiments, the subject to be treated with one of the methods provided herein has not been treated with anticancer therapy. In certain embodiments, the subject to be treated with one of the methods provided herein has been treated with anticancer therapy.

The methods provided herein encompass treating a subject regardless of patient's age, although some diseases or disorders are more common in certain age groups. Further provided herein is a method for treating a subject who has undergone surgery in an attempt to treat the disease or condition at issue, as well as the one who have not. Because the subjects with cancer have heterogeneous clinical manifestations and varying clinical outcomes, the treatment given to a particular subject may vary, depending on his/her prognosis.

In certain embodiments, each method provided herein may independently further comprise the step of administering a second therapeutic agent. In one embodiment, the second therapeutic agent is an anticancer agent. In one embodiment, the anticancer agent is an antimetabolite, including, but not limited to, cytarabine (also known as cytosine arabinoside or Ara-C), fludarabine, 5-fluorouracil, gemcitabine, HDAC (high dose cytarabine), 6-mercaptopurine, methotrexate, and pemetrexed. In another embodiment, the anticancer agent is an antimicrotubule agent, including, but not limited to, vinca alkaloids (e.g., vinblastine, vincristine, and vinorelbine) and taxanes (e.g., paclitaxel, albumin-bound paclitaxel (ABRAXANE®), and docetaxel). In yet another embodiment, the anticancer agent is an alkylating agent, including, but not limited to, busulfan, carmustine, chlorambucil, cyclophosphamide, fludarabine, ifosfamide, mechlorethamine, melphalan, and nitrosoureas (e.g., bischloroethylnitrosurea, hydroxyurea, carmustine, and lomustine). In yet another embodiment, the anticancer agent is a platinum agent, including, but not limited to, carboplatin, CI-973, cisplatin, oxaliplatin, and satraplatin (JM-216). In yet another embodiment, the anticancer agent is an anthracycline, including, but not limited to, adriamycin, daunorubicin, and doxrubicin. In yet another embodiment, the anticancer agent is an antitumor antibiotic, including, but not limited to, adriamycin, bleomycin, daunomycin (also known as daunorubicin), doxorubicin, idarubicin, and mitomycin. In yet another embodiment, the anticancer agent is a topoisomerase inhibitor, including, but not limited to, camptothecins, etoposide, irinotecan, and topotecan. In yet another embodiment, the anticancer agent is a kinase inhibitor, including, but not limited to, erlotinib and imatinib. In yet another embodiment, the anticancer agent is a nucleoside, including, but not limited to, gemcitabine. In yet another embodiment, the anticancer agent is selected from the group consisting of enzymes (asparaginase), hormones (tamoxifen, leuprolide, flutamide, and megestrol), hydroxyurea, interferons, and oblimersen. In still another embodiment, the anticancer agent is a monoclonal antibody, including, but not limited to bevacizumab and cetuximab. For a more comprehensive discussion of updated cancer therapies; See, http://www.nci.nih.gov/, a list of the FDA approved oncology drugs at http://wwwfda.gov/cder/cancer/druglistframe.htm, and The Merck Manual, Seventeenth Ed. 1999, the entire contents of which are hereby incorporated by reference.

The route of administration of the salt provided herein is independent of the route of administration of a second therapy. In one embodiment, the salt provided herein is administered orally. In another embodiment, the salt provided herein is administered intravenously. Thus, in accordance with these embodiments, the salt provided herein is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, the salt provided herein and a second therapy are administered by the same mode of administration, orally or by IV. In another embodiment, the salt provided herein is administered by one mode of administration, e.g., orally, whereas the second agent (an anticancer agent) is administered by another mode of administration, e.g., by IV.

Other therapies or anticancer agents that may be used in combination with the compound provided herein include surgery, radiotherapy, endocrine therapy, biologic response modifiers (e.g., interferons, interleukins, and tumor necrosis factor (TNF)), hyperthermia and cryotherapy, and agents to attenuate any adverse effects (e.g., antiemetics).

In yet another embodiment, provided herein is a method of inhibiting the growth of a cell, comprising contacting the cell with an effective amount of a hydrobromide salt of (4-fluorophenyl)(4-(5-methyl-1H-pyrazol-3-ylamino)quinazolin-2-yl)methanol, or a hydrate or pharmaceutically acceptable solvate thereof, or a crystalline form thereof, including Forms A, B, C, D, E, and F.

In certain embodiments, the cell is a mammalian cell. In certain embodiments, the mammal is a human cell. In certain embodiments, the cell is a tumor cell. In certain embodiments, the cell is mammalian tumor cell. In certain embodiments, the cell is a human tumor cell. In certain embodiments, the cell is a cancerous cell. In certain embodiments, the cell is mammalian cancerous cell. In certain embodiments, the cell is a human cancerous cell.

In certain embodiments, the cancerous cell that can be treated with the methods provided herein includes, but is not limited to, cells of bladder cancer, breast cancer, cervical cancer, colon cancer (e.g., colorectal cancer), endometrial cancer, esophageal cancer, gastric cancer, glioma (e.g., glioblastoma), head and neck cancer, liver cancer, lung cancer (e.g., small cell and non-small cell lung cancers), melanoma, myeloma, neuroblastoma, ovarian cancer, pancreatic cancer, prostate cancer, renal cancer, sarcoma (e.g., osteosarcoma), skin cancer (e.g., squamous cell carcinoma), stomach cancer, testicular cancer, thyroid cancer, and uterine cancer.

In certain embodiments, the cell is a cell of bladder cancer, breast cancer, cervical cancer, colon cancer (e.g., colorectal cancer), endometrial cancer, gastric cancer, glioma (e.g., glioblastoma), head and neck cancer, liver cancer, non-small cell lung cancer, ovarian cancer, pancreatic cancer, or prostate cancer.

The inhibition of cell growth can be gauged by, e.g., counting the number of cells contacted with a compound of interest, comparing the cell proliferation with otherwise identical cells not contacted with the compound, or determining the size of the tumor that encompasses the cells. The number of cells, as well as the size of the cells, can be readily assessed using any method known in the art (e.g., trypan blue exclusion and cell counting, measuring incorporation of $^3$H-thymidine into nascent DNA in a cell).

In yet another embodiment, provided herein is a method of modulating the activity of a JAK kinase, comprising contacting the JAK kinase with a hydrobromide salt of (4-fluorophenyl)(4-(5-methyl-1H-pyrazol-3-ylamino)quinazolin-2-yl) methanol, or a hydrate or pharmaceutically acceptable solvate thereof, or a crystalline form thereof, including Forms A, B, C, D, E, and F. In certain embodiments, provided herein is a method of inhibiting the activity of a JAK kinase, comprising contacting the JAK kinase with a hydrobromide salt of (4-fluorophenyl)(4-(5-methyl-1H-pyrazol-3-ylamino) quinazolin-2-yl)methanol, or a hydrate or pharmaceutically acceptable solvate thereof. In certain embodiments, the JAK kinase is constitutively activated. In certain embodiments, the JAK kinase is mutated.

The salt provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes containers and dosage forms of the salt provided herein.

In certain embodiments, the kit includes a container comprising dosage forms of the salt provided herein, in one or more containers.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); L (liter); mM (millimolar); µM (micromolar); Hz (Hertz); MHz (megahertz); mmol (millimoles); eq. (equivalent); hr or hrs (hours); min (minutes); MS (mass spectrometry); NMR (nuclear magnetic resonance); ESI (electrospray ionization); DSC (differential scanning calorimetry); OM (optical microscopy); TGA (thermogravimetric analysis); XRPD (X-ray powder diffraction); API (active pharmaceutical ingredient); RT (room temperature); ACN, (acetonitrile); tBuOH (tert-butanol); CHCl$_3$ (chloroform); DCM (dichloromethane); DMF (N,N-dimethylformamide); DMSO (dimethylsulfoxide); EtOAc (ethyl acetate); EtOH (ethanol); HEIPA (hexafluoroisopropanol); IPA (isopropanol); IPE (isopropyl ether); MCH (methylcyclohexane); MEK (methyl ethyl ketone); MeOH (methanol); MTBE (methyl tert-butyl ether); TFE (2,2,2-trifluoroethanol); THF (tetrahydrofuran); Me (methyl); Et (ethyl); iPr, (isopropyl); tBu (tert-butyl); Boc (tert-butoxylcarbony); and Bn (benzyl).

For all of the following examples, standard work-up and purification methods known to those skilled in the art can be utilized. Unless otherwise indicated, all temperatures are expressed in ° C. (degrees Centigrade). All procedures were conducted at room temperature unless otherwise noted. Methodologies presented herein are intended to exemplify the applicable chemistry through the use of specific examples and are not indicative of the scope of the disclosure.

For NMR spectra, all samples were prepared in deuterated DMSO. Coupling constants (J) are in Hertz (Hz) and peaks are listed relative to TMS (δ 0.00 ppm).

X-ray powder diffraction analyses were performed using an Inel XRG-3000 diffractometer equipped with a CPS (Curved Position Sensitive) detector with a 2θ range of 120°. Real time data were collected using CuKα radiation at a resolution of 0.03° 2θ. The tube voltage and amperage were set to 40 kV and 30 mA, respectively. The monochromator slit was set at 5 mm by 160 µm. The pattern is displayed from 2.5-40° 2θ. Samples were prepared into thin-walled glass capillaries for analysis. Each capillary was mounted onto a goniometer head that was motorized to permit spinning of the capillary during data acquisition. The samples were analyzed for 300 seconds. Instrument calibration was performed using a silicon reference standard.

XRPD patterns of samples in a 96-well plate were collected with a Bruker D-8 Discover diffractometer and Bruker's General Area Diffraction Detection System (GADDS, v. 4.1.20). An incident beam of CuKα radiation was produced using a fine-focus tube (40 kV, 40 mA), a Gobel mirror, and a 0.5 mm double-pinhole collimator. The samples were positioned for analysis by securing a well plate to a translation stage and moving each sample to intersect the incident beam. The samples were analyzed using transmission geometry. The incident beam was scanned over each sample during the analysis to optimized orientation statistics. A beam-stop was used to minimize air scatter from the incident beam at low angles. Diffraction patterns were collected using a Hi-Star area detector located 15 cm from the sample and processed using GADDS. The intensity in the GADDS image of the diffraction pattern was integrated using a step size of 0.04° 2θ. The integrated patterns display diffraction intensity as a function of 2θ. Prior to the analysis, a silicon standard was analyzed to verify the Si 111 peak position.

XRPD analyses were collected using a PANalytical X'Pert Pro diffractometer. Samples were analyzed using Cu radiation produced using an Optix long fin-focus source. An elliptically graded multilayer mirror was used to focus the CuKα X-rays of the source through the specimen and onto the detector. The specimen was sandwiched between 3-micron thick films, analyzed in transmission geometry, and rotated to optimize orientation statistics. A beam-stop was used to minimize the background generated by air scattering. Helium and antiscatter extension were used. Soller slits were used for the incident and diffracted beams to minimize axial divergence. The diffraction patterns were collected using a scanning position-sensitive detected (X'Celerator) located 240 mm from the specimen. Prior to the analysis a silicon specimen (NIST standard reference material 640c) was analyzed to verify the position of the silicon 111 peak.

Differential scanning calorimetry (DSC) was performed using a TA Instruments differential scanning calorimeter Q2000. Each sample was placed in an aluminum DSC pan, and its weight was accurately recorded. Hermetically sealed laser pin hole or lid covered and crimped pan was used. The sample cell was equilibrated at −30° C. and heated under a nitrogen purge at a rate of 10° C./min, up to a final temperature of 200° C. or 250° C. Indium metal was used as the calibration standard. Reported temperatures are at the transition maxima.

The thermogravimetric analyses (TGA) were performed using a TA Instruments Q5000IR termogravimetric analyzer. Each sample was placed in an aluminum sample pan, inserted into a TG furnace, and accurately weighed. The furnace was heated from ambient temperature under nitrogen at a rate of 10° C./min, up to a final temperature of 350° C. Nickel and ALUMEL™ were used as the calibration standards.

Moisture soption/desorption data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 min, with a maximum equilibration time of 3 hrs if the weight criterion was not met. Data were not corrected for the initial moisture content of the samples. NaCl and PVP were used as calibration standards.

Elemental analysis for carbon, hydrogen, nitrogen, and bromine was performed by Robertson Microlit Laboratory (Madison, N.J.).

Hot stage microscopy was performed using a Linkam FTIR 600 hot stage mounted on an Olympus BX51 microscope. Temperature readings were taken from the thermocouple. Samples were placed on a cover glass, and a second cover glass was placed on top of the sample. As the stage was heated, each sample was visually observed using a 10×objective with crossed polarizers. Observations were visual.

Example 1

Preparation of hydrobromide salts of 4-fluorophenyl) (4-(5-methyl-1H-pyrazol-3-ylamino)quinazolin-2-yl) methanol A mixture of (4-fluorophenyl)(4-(5-methyl-1H-pyrazol-3-ylamino)quinazolin-2-yl)methanol (260 g, 0.744 mol) and ethanol (2.86 L) in a round bottom flask under nitrogen was heated at reflux for 30 to 40 min, and then 48% aq. HBr (125.5 g, 0.744 mmol) was added while maintaining reflux. The mixture was allowed to cool to 25-30° C., and the mixture was stirred at 25-30° C. for 1 hr. The solid was collected by filtration, washing thoroughly with fresh ethanol (0.52 L). The solid was dried at 55 to 65° C. for 12 to 14 hrs to afford (4-fluorophenyl)(4-(5-methyl-1H-pyrazol-3-ylamino) quinazolin-2-yl)methanol hydrobromide (276 g, 86%). HPLC (AUC) 99.9%.

Example 2

Characterization of Form A

Form A was characterized by X-ray powder diffraction (XRPD), thermogravimetry (TG), differential scanning calorimetry (DSC), moisture sorption analysis, hotstage microscopy, and proton nuclear magnetic resonance spectroscopy ($^1$H NMR). Overall, the HBr salt of Form A is consistent with a crystalline salt of the compound of Formula I, containing residual solvent(s).

A representative XRPD pattern of crystalline Form A is shown in FIG. 1. Some XRPD peaks of crystalline Form A are summarized in Table I.

TABLE I

| X-Ray Diffraction Peaks for Form A | | |
|---|---|---|
| Two-theta angle (°) | d Space (Å) | Intensity (%) |
| 7.48 ± 0.10 | 11.816 ± 0.160 | 100 |
| 9.29 ± 0.10 | 9.523 ± 0.103 | 6 |
| 10.82 ± 0.10 | 8.174 ± 0.076 | 12 |
| 11.30 ± 0.10 | 7.830 ± 0.070 | 6 |
| 13.07 ± 0.10 | 6.773 ± 0.052 | 1 |
| 13.34 ± 0.10 | 6.638 ± 0.050 | 2 |
| 13.97 ± 0.10 | 6.338 ± 0.045 | 1 |
| 14.60 ± 0.10 | 6.067 ± 0.042 | 4 |
| 14.83 ± 0.10 | 5.975 ± 0.040 | 10 |
| 15.85 ± 0.10 | 5.590 ± 0.035 | 2 |
| 16.55 ± 0.10 | 5.357 ± 0.032 | 5 |
| 16.98 ± 0.10 | 5.221 ± 0.031 | 2 |
| 18.07 ± 0.10 | 4.910 ± 0.027 | 5 |
| 18.70 ± 0.10 | 4.744 ± 0.025 | 6 |
| 20.12 ± 0.10 | 4.413 ± 0.022 | 1 |
| 20.92 ± 0.10 | 4.247 ± 0.020 | 9 |
| 21.21 ± 0.10 | 4.189 ± 0.020 | 3 |
| 21.50 ± 0.10 | 4.133 ± 0.019 | 20 |
| 21.90 ± 0.10 | 4.058 ± 0.018 | 14 |
| 22.05 ± 0.10 | 4.031 ± 0.018 | 13 |
| 22.71 ± 0.10 | 3.915 ± 0.017 | 15 |
| 23.03 ± 0.10 | 3.862 ± 0.017 | 5 |
| 23.32 ± 0.10 | 3.814 ± 0.016 | 3 |
| 23.96 ± 0.10 | 3.714 ± 0.015 | 7 |
| 25.64 ± 0.10 | 3.475 ± 0.013 | 1 |
| 26.09 ± 0.10 | 3.416 ± 0.013 | 5 |
| 26.43 ± 0.10 | 3.372 ± 0.013 | 16 |
| 26.67 ± 0.10 | 3.343 ± 0.012 | 13 |
| 26.88 ± 0.10 | 3.317 ± 0.012 | 5 |
| 27.69 ± 0.10 | 3.222 ± 0.011 | 1 |

TABLE I-continued

X-Ray Diffraction Peaks for Form A

| Two-theta angle (°) | d Space (Å) | Intensity (%) |
|---|---|---|
| 28.19 ± 0.10 | 3.166 ± 0.011 | 6 |
| 28.51 ± 0.10 | 3.131 ± 0.011 | 8 |
| 29.26 ± 0.10 | 3.053 ± 0.010 | 3 |
| 29.90 ± 0.10 | 2.988 ± 0.010 | 3 |

XRPD data exhibited resolution of peaks indicative of crystalline material. The XRPD pattern was successfully indexed, indicating the sample is composed primarily of a single crystalline phase. The space group consistent with the assigned extinction symbol, as well as the unit cell parameters and derived quantities are tabulated in Table II. Because the compound of Formula I is a racemate, both P1 (#1) and P-1 (#2) are possible space groups for the unit cell of the HBr salt. These space groups cannot be distinguished based on indexing alone.

Thermogravimetric data show a ~0.4 wt % loss between ~25° C. and ~114° C., followed by a ~0.3 wt % loss between ~142° C. and ~218° C. Both weight losses may be due to the release of residual solvents, possibly ethanol and/or water. At ~259° C. (onset), a sharp weight loss occurs, likely attributable to decomposition.

TABLE II

| Molecular Formula | $C_{19}H_{16}FN_5O \cdot HBr$ | | | |
|---|---|---|---|---|
| Crystal System | Triclinic | | | |
| Space Group | P1 or | a | 8.554 Å | α 77.32° |
| | P-1 | b | 9.753 Å | β 72.71° |
| | | c | 12.610 Å | γ 83.96° |
| V | 979.06 Å³ | | | |
| V/Z (Å³/cell) | 489.5 | | | |
| Z'/Z | 2/2 or 1/2 | | | |
| $D_c$ | 1.46 g/cm³ | | | |

The DSC thermogram exhibited a strong broad endotherm at ~274.2° C. (peak maximum), attributable to decomposition.

Moisture sorption data are consistent with a limited hygroscopic material. Data show a ~0.3 wt % loss upon equilibration at ~5% RH. A 1.0 wt % gain is observed upon an increase in relative humidity from ~5% and ~95% RH. A ~1.0 wt % loss was observed upon a decrease in relative humidity from ~95% and ~5% RH.

Proton nuclear magnetic resonance ($^1$H NMR) chemical shifts in the region ~7.0-8.5 ppm and integral values are overall consistent with a salt of the compound of Formula I. The peak at ~1.06 ppm is likely attributable to ~0.02 moles of ethanol per mole of the compound of Formula I.

Hotstage microscopy was performed on the HBr salt of Form A under dry conditions as well as using mineral oil. Under both conditions, hotstage microscopy of the HBr salt revealed no physical changes in the material prior to melting. The material melted between ~218 and ~228° C. Quench cooling the material using dry ice resulted in brown solids indicating decomposition at melting. Warming the material back to room temperature resulted in a brown oil.

Additional thermal microscopy studies were performed using various solvents to assess any changes in physical morphology (Table III). Six experiments were performed in which a small amount of the HBr salt of Form A was dissolved in hexafluoroisopropanol or dimethylsulfoxide followed by heating to evaporate the solvent. In five of the six experiments, the solvent was quickly removed followed by cooling the slide over dry ice in an attempt to form a glass. In one experiment, the solvent was slowly removed by gradual heating. Removing hexafluoroisopropanol slowly or quickly resulted in white solids of unknown morphology demonstrating birefringence and extinction. Evaporating dimethylsulfoxide followed by crash cooling over ice resulted in a glass. Addition of solvent (methanol, water, or toluene) and vapor stress at elevated temperature, however, did not appear to visually crystallize the glass.

TABLE III

| Condition | Temp (° C.) | Heating Rate (° C./min) | Observation |
|---|---|---|---|
| Form A (dry) | 23 | 20 | Needles |
| | 90 | 5 | No change |
| | 103 | 5 | — |
| | 105 | 5 | No sublimation |
| | 180 | 20 | No change |
| | 218 | 5 | Onset of melt |
| | 228 | 5 | Melt complete |
| | — | Cooled over dry ice | Brownish solids |
| | 23 | — | Brown oil |
| Form A under mineral oil | 22 | 20 | Rods |
| | 88 | 20 | No change |
| | 165 | 20 | No change |
| | 200 | 5 | No change |
| | 219 | 5 | Onset of melt |

Example 3

Solubility of Form A

The solubility of the HBr salt of Form A in selected solvents was estimated by solvent addition under ambient conditions to provide preliminary information for the polymorph screen. As shown in Table IV, the HBr salt was freely soluble in a hexafluoroisopropanol (>128 mg/mL) and in dimethylformamide (>114 mg/mL). This material is sparingly soluble in methanol, methanol/chloroform (1:1), and methanol/tetrahydrofuran (~14-20 mg/mL). It was estimated to be slightly soluble in ethanol, 2,2,2-trifluoroethanol, and 1:1 mixture of t-butanol/water (~3-7 mg/mL), and exhibited a solubility below ~2 mg/mL in acetone, acetonitrile, chloroform, dichloromethane, ethyl acetate, isopropyl alcohol, nitromethane, tetrahydrofuran, toluene, water, and mixtures of dimethylformamide/water (1:4 and 1:9).

TABLE IV

| Solvent | Solubility (mg/mL) |
|---|---|
| Acetone | <2 |
| ACN | <2 |
| Chloroform | <2 |
| DCM | <2 |
| DMF | >114 |
| EtOH | 3 |
| EtOAc | <2 |
| HFIPA | >128 |
| IPA | <2 |
| MeOH | 18 |
| Nitromethane | <2 |
| TFE | 7 |
| THF | <2 |
| Toluene | <2 |
| Water | <2 |
| t-Butanol/water (1:1) | 7 |
| t-Butanol/water (3:1) | 6 |
| DMF/water (1:1) | 30 |
| DMF/water (1:2) | 4 |

TABLE IV-continued

| Solvent | Solubility (mg/mL) |
| --- | --- |
| DMF/water (1:4) | <2 |
| DMF/water (1:9) | <2 |
| MeOH/chloroform (1:1) | 16 |
| MeOH/THF (1:1) | 14 |

Example 4

Polymorph screening of a hydrobromide salt of 4-fluorophenyl)(4-(5-methyl-1H-pyrazol-3-ylamino) quinazolin-2-yl)methanol a. Evaporation Solutions generated at ambient temperature were allowed to evaporate to dryness either from an open well plate (fast evaporation, FE) or from a well plate covered with aluminum foil containing a pinhole (slow evaporation, SE).

b. Rotary Evaporation

Solutions were generated at ambient temperature and filtered. The solvents were then removed using a rotary evaporator (RE) at elevated temperature.

c. Cooling of a Solution Experiments

Solutions containing hydrobromide salt of 4-fluorophenyl) (4-(5-methyl-1H-pyrazol-3-ylamino)quinazolin-2-yl) methanol in crystalline Form A were prepared at elevated temperature, hot filtered, and allowed to cool down to room temperature either by turning the heating device off (slow cooling, SC), placing filtered solutions on an ambient stirring plate (fast cooling, FC) or hot filtering samples into chilled containers (crash cooling, CC). Solids that formed were isolated by vacuum filtration.

d. Solvent Anti-Solvent Experiments

Solutions were generated by addition of a solvent or solvent mixture at ambient temperature and filtered. An excess of anti-solvent was added. Precipitated solids were isolated by vacuum filtration.

e. Slurry Experiments

Slurries were prepared by adding a solvent or solvent mixture to hydrobromide salt of 4-fluorophenyl)(4-(5-methyl-1H-pyrazol-3-ylamino)quinazolin-2-yl)methanol in crystalline Form A. The mixtures were then agitated in a sealed vial at either ambient or a set temperature. After a given amount of time, the solids were isolated by vacuum filtration.

f. Vapor Diffusion

Vapor diffusion experiments were performed by dissolving hydrobromide salt of 4-fluorophenyl)(4-(5-methyl-1H-pyrazol-3-ylamino)quinazolin-2-yl)methanol in crystalline Form A in a solvent or solvent mixture and placing the vial containing the solution in an enclosed chamber containing an anti-solvent.

g. Heat and Vapor Stress Experiments

Samples were placed in a RH jar of specified relative humidity at ambient temperature or elevated temperature for a given amount of time. Samples were placed in heating/vacuum oven at specified temperature for thermal stressing.

In summary, Form A was obtained in the majority of experiments. Three other crystalline materials exhibiting distinct XRPD patterns were obtained, designated as Forms C, D, and E. Two additional crystalline forms, designated as Forms B and F, were isolated as mixtures with Form A. Table V summarizes the conditions of preparation of various crystalline forms.

Two attempts were made to prepare amorphous HBr salt of the compound of Formula I for use during microscale and medium scale experiments. The first attempt by rotary evaporation of the HBr salt from hexafluoroisopropanol at elevated temperature resulted in material designated as disordered Form A plus Form F based on XRPD results. This disordered mixture was one of the starting materials for the microscale experiments. No further characterization was performed on this disordered mixture of Form A and Form F.

TABLE V

| Form | Conditions of Preparation | Additional Information |
| --- | --- | --- |
| B | Hexafluoroisopropanol/ACN (Solvent/Anti-solvent) | Vacuum drying resulted in material primarily consistent with Form A and a minor amount of Form B |
| C | Cool from methanol/toluene (1:1) | Data consistent with a toluene solvate of the HBr salt containing about 0.4 to 0.5 moles of toluene per mole of the HBr salt. Vacuum drying resulted in a mixture of Forms A and C. |
| D | Slurry in ethanol at about 40° C. and cool from ethanol/water (4:1). | Similar to XRPD pattern of Form A. Vacuum drying resulted in Form A. |
| E | Slurry of mixture of Forms A and E in DMF/water (1:3) at about 40° C. | Indexing and NMR data suggest that Form E is a free base. Form E remained the same after vacuum drying. |
| F | Rotary evaporation from hexafluoroisopropanol | Form F was isolated as a mixture with Form A. Peaks in an XRPD pattern attributable to Form F are similar to these of Form C. |

A second attempt to prepare amorphous HBr salt of the compound of Formula I by freeze drying from t-butanol/water (1:1) resulted in material designated as disordered Form A based on XRPD results. This disordered material was used for a limited number of medium scale experiments.

The results of a polymorph screen of the HBr salt conducted in a 96-well plate at microscale as well as at medium scale are presented in Tables VI-XIII. Solid material isolated during the screen was analyzed by XRPD.

TABLE VI

| Solvent | Conditions | Observation |
| --- | --- | --- |
| HFIPA | Dissolved in the solvent, heated quickly on hot bench at 110° C., and cooled over dry ice | White solids, unknown morphology |
| HFIPA | Dissolved in the solvent and heated gradually on hot bench | White solids, unknown morphology |
| DMSO/MeOH | Dissolved in DMSO, quickly heated on hot bench, and cooled over dry ice Added drop MeOH, evaporated at RT 40% RH stress at 50° C. for 4 days | Yellow glass |
| DMSO/MeOH | Dissolved in DMSO, quickly heated on hot bench, and cooled over dry ice Added drop MeOH, evaporated at dry ice 40% RH stress at 50° C. for 4 days | Yellow glass |
| DMSO/water | Dissolved in DMSO, quickly heated on hot bench, and cooled over dry ice Added drop water, evaporated at RT 40% RH stress at 50° C. for 4 days | Yellow glass |
| DMSO/toluene | Dissolved in DMSO, quickly heated on hot bench, and cooled over dry ice Added drop toluene, evaporated over dry ice 40% RH stress at 50° C. for 4 days | Yellow glass |

Polymorph Screen at Microscale (96-well plate)

The 96-well plate was divided into four zones based on crystallization technique: (i) slow evaporation from solution (Table VII), (ii) fast evaporation from solution (Table VIII), (iii) slow evaporation from a slurry of disordered material (Table IX), and (iv) fast evaporation from a slurry of disordered material (Table X). A variety of solvents and solvent mixtures was used to vary the crystallization conditions.

Approximately two-thirds of the microscale experiments resulted in material consistent with Form A. The remaining wells resulted in two new materials designated as Form B and Form C or mixtures of these materials and Form A. Results indicate that Form B was not isolated as a pure material.

Mixtures of Forms A and B were obtained under the following experimental conditions: slow or fast evaporation from a 1:1 mixture of hexafluoroisopropanol/acetonitrile, hexafluoroisopropanol/nitromethane, or hexafluoroisopropanol/water.

Form C was obtained from slow evaporation of a 2:1 mixture of methanol/toluene. Mixtures of Form A and Form C were also obtained from solvent mixtures containing toluene. XRPD results also indicate mixtures of Forms A and F from several experimental conditions and solvent mixtures. Two experiments from a slow evaporation of a slurry in tetrahydrofuran and a 1:1 mixture of tetrahydrofuran and ethanol resulted in material mainly consistent with Form A with an additional peak at ~6.8° 2θ observed. A single experiment from slow evaporation of a 2:1 methanol/nitromethane mixture resulted in material exhibiting an XRPD pattern identical to Form A with one extra peak at ~19.1° 2θ.

TABLE VII

Polymorph screen of the HBr salt using Form A as starting material (Microscale slow evaporation)

| Solvent | Observations | XRPD Results |
| --- | --- | --- |
| HFIPA/ACN (1:1) | Unknown morphology, opaque aggregates | Forms A + B |
| HFIPA/EtOH (1:1) | Unknown morphology, opaque aggregates | Forms A + F |
| HFIPA/heptane (1:1) | Unknown morphology, opaque aggregates | Forms A + F |
| HFIPA/IPA (1:1) | Unknown morphology, opaque aggregates | Forms A + F |
| HFIPA/THF (1:1) | Unknown morphology, opaque aggregates | Forms A + F |
| HFIPA/nitromethane (1:1) | Unknown morphology, rods | Forms A + B |
| HFIPA/CHCl$_3$ (1:1) | Unknown morphology, opaque aggregates | Forms A + F |
| HFIPA/EtOAc (1:1) | Unknown morphology, opaque aggregates | Forms A + F |
| HFIPA/IPE (1:1) | Unknown morphology, opaque aggregates | Forms A + F |
| HFIPA/MEK (1:1) | Unknown morphology, opaque aggregates | Form A |
| HFIPA/toluene (1:1) | Unknown morphology, opaque aggregates | Forms A + F |
| HFIPA/water (1:1) | Unknown morphology, plates | Forms A + B |
| MeOH/ACN (2:1) | Unknown morphology, rods | Form A |
| MeOH/EtOH (2:1) | Unknown morphology, rods | Form A |
| MeOH/heptane (2:1) | Unknown morphology, rods | Form A |
| MeOH/IPA (2:1) | Unknown morphology, needles | Form A |
| MeOH/THF (2:1) | Unknown morphology, rods | Form A |
| MeOH/nitromethane (2:1) | Unknown morphology, rods | Form A + peak at ~19.1 °2θ |
| MeOH/CHCl$_3$ (2:1) | Unknown morphology, rods | Form A |
| MeOH/EtOAc (2:1) | Unknown morphology, rods | Form A |
| MeOH/IPE (2:1) | Unknown morphology, opaque aggregates | Form A |
| MeOH/MEK (2:1) | Unknown morphology, rods | Form A |
| MeOH/toluene (2:1) | Unknown morphology, opaque aggregates | Form C |
| MeOH/water (2:1) | Unknown morphology, rods | Form A |

TABLE VIII

Polymorph screen of the HBr salt using Form A as starting material (Microscale fast evaporation)

| Solvent | Observations | XRPD Results |
| --- | --- | --- |
| HFIPA/ACN (1:1) | Unknown morphology, opaque aggregates | Forms A + B |
| HFIPA/EtOH (1:1) | Unknown morphology, rods | Forms A + F |
| HFIPA/heptane (1:1) | Unknown morphology, opaque aggregates | Forms A + F |
| HFIPA/IPA (1:1) | Unknown morphology, opaque aggregates | Forms A + F |
| HFIPA/THF (1:1) | Unknown morphology, opaque aggregates | Forms A + F |
| HFIPA/nitromethane (1:1) | Unknown morphology, needles | Forms A + B |
| HFIPA/CHCl$_3$ (1:1) | Unknown morphology, plates | Forms A + F |
| HFIPA/EtOAc (1:1) | Unknown morphology, opaque aggregates | Forms A + F |
| HFIPA/IPE (1:1) | Unknown morphology, opaque aggregates | Forms A + F |
| HFIPA/MEK (1:1) | Unknown morphology, opaque aggregates | Form A |
| HFIPA/toluene (1:1) | Unknown morphology, opaque aggregates | Forms A + C |
| HFIPA/water (1:1) | Unknown morphology, opaque aggregates | Forms A + B |
| MeOH/ACN (2:1) | Unknown morphology, rods | Form A |
| MeOH/EtOH (2:1) | Unknown morphology, rods | Form A |
| MeOH/heptane (2:1) | Unknown morphology, rods | Form A |
| MeOH/IPA (2:1) | Unknown morphology, rods | Form A |
| MeOH/THF (2:1) | Unknown morphology, rods | Form A |
| MeOH/nitromethane (2:1) | Unknown morphology, rods | Form A + peak at ~19.1 °2θ |
| MeOH/CHCl$_3$ (2:1) | Unknown morphology, needles | Form A |
| MeOH/EtOAc (2:1) | Unknown morphology, rods | Form A |
| MeOH/IPE (2:1) | Unknown morphology, opaque aggregates | Form A |
| MeOH/MEK (2:1) | Unknown morphology, rods | Form A |
| MeOH/toluene (2:1) | Unknown morphology, opaque aggregates | Forms A + C |
| MeOH/water (2:1) | Unknown morphology, rods | Form A |

TABLE IX

Polymorph screen of the HBr salt using disordered Form A as starting material (Microscale slurry/slow evaporation)

| Solvent | Observations | XRPD Results |
| --- | --- | --- |
| Acetone/EtOH (1:1) | Unknown morphology, opaque aggregates | Form A |
| CHCl$_3$/TFE (1:1) | Unknown morphology, opaque aggregates | Form A |
| Nitromethane/ACN (1:1) | Unknown morphology, opaque aggregates | Form A |
| Acetone/water (1:1) | Unknown morphology, rods | Form A |
| Acetone | Unknown morphology, opaque aggregates | Form A |
| IPE | Unknown morphology, opaque aggregates | Form A |
| EtOAc/EtOH (1:1) | Unknown morphology, opaque aggregates | Form A |
| ACN/TFE (1:1) | Unknown morphology, opaque aggregates | Form A |
| Water/ACN (1:1) | Unknown morphology, opaque aggregates | Form A |
| THF/water (1:1) | Unknown morphology, needles | Form A |
| CHCl$_3$ | Unknown morphology, opaque aggregates | Form A |
| IPA | Unknown morphology, opaque aggregates | Form A |
| THF/EtOH (1:1) | Unknown morphology, opaque aggregates | Form A + a peak at ~6.8 °2θ |
| MEK/TFE (1:1) | Unknown morphology, opaque aggregates | Form A |

TABLE IX-continued

Polymorph screen of the HBr salt using disordered Form A as starting material (Microscale slurry/slow evaporation)

| Solvent | Observations | XRPD Results |
|---|---|---|
| Heptane/ACN (1:1) | Unknown morphology, opaque aggregates | Form A |
| EtOH/water (1:1) | Unknown morphology, opaque aggregates | Form A |
| EtOH | Unknown morphology, opaque aggregates | Form A |
| Heptane | Unknown morphology, opaque aggregates | Form A |
| Toluene/EtOH (1:1) | Unknown morphology, opaque aggregates | Forms A + C |
| IPE/TFE (1:1) | Unknown morphology, opaque aggregates | Form A |
| IPA/ACN (1:1) | Unknown morphology, opaque aggregates | Form A |
| IPA/water (1:1) | Unknown morphology, opaque aggregates | Form A |
| THF | Unknown morphology, opaque aggregates | Form A + peak at ~6.8 °2θ |
| MEK | Unknown morphology, opaque aggregates | Form A |

TABLE X

Polymorph screen of the HBr salt using disordered Form A as starting material (Microscale slurry/fast evaporation)

| Solvent | Observations | XRPD Results |
|---|---|---|
| Acetone/EtOH (1:1) | Unknown morphology, opaque aggregates | Form A |
| CHCl₃/TFE (1:1) | Unknown morphology, opaque aggregates | Form A |
| Nitromethane/ACN (1:1) | Unknown morphology, opaque aggregates | Form A |
| Acetone/water (1:1) | Unknown morphology, needles | Form A |
| TFE | Unknown morphology, opaque aggregates | Form A |
| Toluene | Unknown morphology, opaque aggregates | Form A |
| EtOAc/EtOH (1:1) | Unknown morphology, opaque aggregates | Form A |
| ACN/TFE (1:1) | Unknown morphology, opaque aggregates | Form A |
| Water/ACN (1:1) | Unknown morphology, opaque aggregates | Form A |
| THF/water (1:1) | Unknown morphology, needles | Form A |
| ACN | Unknown morphology, opaque aggregates | Form A |
| Nitromethane | Unknown morphology, opaque aggregates | Form A |
| THF/EtOH (1:1) | Unknown morphology, opaque aggregates | Form A |
| MEK/TFE (1:1) | Unknown morphology, opaque aggregates | Form A |
| Heptane/ACN (1:1) | Unknown morphology, opaque aggregates | Form A |
| EtOH/water (1:1) | Unknown morphology, needles | Form A |
| EtOAc | Unknown morphology, opaque aggregates | Form A |
| Water | Unknown morphology, opaque aggregates | Form A |
| Toluene/EtOH (1:1) | Unknown morphology, opaque aggregates | Forms A + C |
| IPE/TFE (1:1) | Unknown morphology, opaque aggregates | Form A |
| IPA/ACN (1:1) | Unknown morphology, opaque aggregates | Form A |
| IPA water (1:1) | Unknown morphology, opaque aggregates | Form A |
| MeOH | Unknown morphology, opaque aggregates | Form A |

Polymorph Screen at Medium Scale

Medium scale experiments were designed using the preliminary information obtained from microscale experiments. A variety of crystallization conditions were performed, targeting the generation of solids under thermodynamic and kinetic conditions of growth. Experiments included cools (slow, fast, and crash cools), solvent/anti-solvent precipitations, vapor diffusion with an anti-solvent, and slurries at elevated and ambient temperature in a variety of solvents and solvent mixtures. Form A or disordered Form A of the HBr salt were used as the starting materials.

All solids isolated in sufficient quantity were analyzed by X-ray powder diffraction. Table XI summarizes the experiments performed using Form A, whereas Table XII summarizes the experiments performed using various forms of the HBr salt. Table XIII summarizes the conditions for scale-up experiments targeting two materials.

TABLE XI

Polymorph screen of the HBr salt using Form A as starting material

| Solvent | Conditions | Observations | XRPD Results |
|---|---|---|---|
| tBuOH/water (1:1) | Slow cooling from ~70° C. to RT, stirred at RT for ~3 days | Unknown morphology, opaque aggregates | Form A + minor Form E |
| tBuOH/water (1:2) | Slow cooling from ~70° C. to RT, stirred at RT for ~3 days, vacuum filtration (some solids deliquesced) | Unknown morphology, opaque aggregates | Form A + minor Form E |
| DMF/CHCl₃ | Vapor diffusion | Plate-like structures, rods | Form A |
| DMF/water | Solvent/antisolvent precipitation, slurry at RT for ~1 day, vacuum filtration (some solids deliquesced) | Unknown morphology, opaque aggregates | Form A + minor Form E |
| DMF/ACN (1:2) | Fast cooling from ~78° C. to RT (clear), kept in freezer for ~8 days | Clear solution | — |
| DMF/water (~1:4) | Slow cooling from ~80° C. to RT (solids after ~30 min), stirred at RT for ~1 day, vacuum filtration (some solids deliquesced) | Unknown morphology, opaque aggregates | Form E (disordered) |
| EtOH | Slurry at ~40° C. for ~4 days | Unknown morphology, opaque aggregates, few rods | Form D |
| EtOH/water (4:1) | Slow cooling from ~70° C. to RT (few needles), kept in refrigerator for ~2 days | Rods | Form D |
| EtOAc | Slurry at ~45° C. for ~4 days | Unknown morphology, opaque aggregates | Form A + a shoulder at ~6.8 °2θ |
| HFIPA/acetone | Solvent/antisolvent precipitation, slurry at RT for ~1 day | Unknown morphology, needles | Form A |
| HFIPA/ACN | Solvent/antisolvent precipitation | Unknown morphology, opaque aggregates | Form A |
| HFIPA/nitromethane | Solvent/antisolvent precipitation | Unknown morphology, opaque aggregates | Forms A + B |
| MeOH/nitromethane (1:1) | Fast cooling from ~60° C. to RT (clear), kept in freezer for ~4 days | Unknown morphology, rods | Form A |

TABLE XI-continued

Polymorph screen of the HBr salt using Form A as starting material

| Solvent | Conditions | Observations | XRPD Results |
|---|---|---|---|
| MeOH/ toluene (1:1) | Fast cooling from ~56° C. to RT (clear), kept in freezer for ~2 days | Unknown morphology, opaque aggregates | Form C |
| THF/ EtOH (1:1) | Crash cooling from ~56° C. to RT (clear), kept in freezer for ~1 day | Unknown morphology, opaque aggregates, few rods | Form A |
| Toluene | Slurry at ~60° C. for ~4 days | Unknown morphology, opaque aggregates | Form C + minor Form A |
| Water | Slurry at ~60° C. for ~5 or ~7 days | Unknown morphology, opaque aggregates | Form A + minor Form E |

TABLE XII

Polymorph screen

| Starting Material | Conditions | Observations | XRPD Results |
|---|---|---|---|
| Disordered Form A | EtOH, slow cooling from ~66° C. to RT | Unknown morphology, opaque aggregates | Form A |
| Disordered Form A | ~94% RH vapor stress at RT for ~3 days | Unknown morphology, opaque aggregates | Disordered A |
| Form C | Vacuum over at ~80° C. for ~1 day | Unknown morphology, opaque aggregates, rods | Forms A + C |
| Form D | Vacuum over at ~40° C. for ~3 days | Unknown morphology, opaque aggregates, rods | Form A |
| Forms A + B | Vacuum over at ~60° C. for ~1 day | Unknown morphology, opaque aggregates | Form A + minor Form B |
| Form E | Vacuum over at ~60° C. for ~2 days | Unknown morphology, opaque aggregates | Form E |

TABLE XIII

Scale-up experiments targeting potential polymorphs of the HBr salt

| Targeted Form | Conditions | Observations | XRPD Results |
|---|---|---|---|
| C | Dissolved API in MeOH/toluene (1:1) at ~56° C., fast cooling from ~56° C. to RT (very few solids), kept in freezer for ~4 days (yield: ~34%) | Unknown morphology, opaque aggregates, rods | Form C |
| E | DMF/water (1:2), slurry at RT for ~7 days, vacuum filtration (washed solids with water during filtration) | Unknown morphology, opaque aggregates | Forms A + E |
|  | DMF/water (1:3), slurry at RT for ~6 days, vacuum filtration (washed solids with water during filtration) | Unknown morphology, opaque aggregates, rods | Forms A + E |
|  | DMF/water (1:3), slurry at RT for ~6 days, vacuum filtration (washed solids with water during filtration) | Unknown morphology, opaque aggregates, rods | Form E |
|  | DMF/water (1:3), slurry at ~40° C. for ~5 days, vacuum filtration (washed solids with water during filtration) | | |
|  | DMF/water (1:3), slurry at ~35° C. for ~4 days, vacuum filtration (washed solids with water during filtration) | Unknown morphology, opaque aggregates | Form E + minor Form A |
|  | DMF/water (1:3), slurry at ~40° C. for ~6 days (thick solution after ~2 days, more solvent added to facilitate slurry), vacuum filtration (washed solids with water during filtration) | Unknown morphology, opaque aggregates | Forms A + E |

Sixteen medium scale experiments have been performed using Form A salt as the starting material. Material consistent with Form A was obtained from five of these experiments: diffusing chloroform into a dimethylformamide solution of the HBr salt, solvent/anti-solvent experiments using hexafluoroisopropanol/acetonitrile and hexafluoroisopropanol/acetone, crash cooling from a 1:1 mixture of tetrahydrofuran and ethanol, fast cooling from a 1:1 mixture of methanol and nitromethane.

Form B was obtained only once as a mixture with Form A from a solvent/anti-solvent experiment using hexafluoroisopropanol/nitromethane.

Pure Form C was obtained exclusively from fast cooling of a solution of the HBr salt in methanol/toluene (1:1). An elevated temperature slurry in toluene resulted in material consistent with Form C with a small amount of Form A.

Form E was obtained as a disordered material from a slow cooling experiment in a dimethylformamide/water mixture. Slurrying Form A in water for approximately 7 days at ~60° C. resulted in material consistent with a mixture of Forms A and E. Two additional experiments containing water resulted in material that was mainly consistent with Form A but may contain a very small amount of Form E.

Form D was obtained from two experiments: elevated temperature slurry in ethanol and an ethanol/water (4:1) slow cooling experiment. XRPD results indicate that Form D is similar to Form A, but significant shifting is observed above 20° 2θ. The similarity between the two XRPD patterns suggests that the two materials may be structurally related.

A slurry in ethyl acetate at ~45° C. resulted in material consistent with Form A with a shoulder at ~6.8° 2θ, similar to a peak observed during the microscale experiments.

Six experiments were performed using the disordered Form A as starting material. The use of disordered Form A prepared by lyophillization resulted in crystalline Form A from a slow cooling experiment in ethanol, but remained disordered upon exposure to ~94% relative humidity for approximately three days. Drying the mixture of Forms A and B under vacuum at ~60° C. for approximately two days resulted in material primarily consistent with Form A with a minor amount of Form B. Drying Form C under vacuum at ~80° C. for approximately one day resulted in a mixture of Forms A and C.

Drying Form D under vacuum at ~40° C. for approximately three days resulted in material consistent with Form A. No changes were observed in the XRPD pattern of Form E after drying under vacuum at ~60° C. for approximately two days.

Form C was prepared at ~400 mg scale using the same method as that used during the medium scale experiments; the yield was ~34%. Five experiments were performed at large scale in an attempt to isolate pure Form E in which solvent ratios, water activities, and temperature were varied. Pure Form E was isolated from a slurry of a mixture of Form A and Form E in a dimethylformamide/water (1:3) solvent system at ~40° C. for approximately five days. Solids were washed with water during filtration with the intent of removing residual dimethylformamide.

Example 5

Characterization of Form C

Form C was characterized by X-ray powder diffraction (XRPD), thermogravimetry (TG), differential scanning calorimetry (DSC), moisture sorption analysis, and proton nuclear magnetic resonance spectroscopy ($^1$H NMR). The characterization data are consistent with a solvated crystalline HBr salt of the compound of Formula I, likely containing toluene.

A representative XRPD pattern of crystalline Form C is shown in FIG. 2. Some XRPD peaks of crystalline Form C are summarized in Table XIV.

TABLE XIV

X-Ray Diffraction Peaks for Form C

| Two-theta angle (°) | d Space (Å) | Intensity (%) |
|---|---|---|
| 6.57 ± 0.10 | 13.447 ± 0.208 | 100 |
| 9.63 ± 0.10 | 9.183 ± 0.096 | 3 |
| 11.89 ± 0.10 | 7.445 ± 0.063 | 2 |
| 12.94 ± 0.10 | 6.842 ± 0.053 | 2 |
| 13.17 ± 0.10 | 6.721 ± 0.051 | 7 |
| 13.49 ± 0.10 | 6.563 ± 0.049 | 1 |
| 15.18 ± 0.10 | 5.837 ± 0.038 | 2 |
| 15.40 ± 0.10 | 5.755 ± 0.037 | 8 |
| 16.18 ± 0.10 | 5.477 ± 0.034 | 13 |
| 16.88 ± 0.10 | 5.251 ± 0.031 | 8 |
| 17.47 ± 0.10 | 5.077 ± 0.029 | 1 |
| 17.65 ± 0.10 | 5.024 ± 0.028 | 1 |
| 18.20 ± 0.10 | 4.873 ± 0.027 | 4 |
| 18.39 ± 0.10 | 4.825 ± 0.026 | 20 |
| 18.62 ± 0.10 | 4.765 ± 0.025 | 2 |
| 19.32 ± 0.10 | 4.593 ± 0.024 | 7 |
| 19.81 ± 0.10 | 4.482 ± 0.023 | 8 |
| 20.01 ± 0.10 | 4.438 ± 0.022 | 6 |
| 20.34 ± 0.10 | 4.365 ± 0.021 | 5 |
| 20.96 ± 0.10 | 4.238 ± 0.020 | 7 |
| 21.30 ± 0.10 | 4.172 ± 0.019 | 4 |
| 21.53 ± 0.10 | 4.128 ± 0.019 | 19 |
| 21.93 ± 0.10 | 4.053 ± 0.018 | 2 |
| 22.30 ± 0.10 | 3.987 ± 0.018 | 13 |
| 22.53 ± 0.10 | 3.946 ± 0.017 | 19 |
| 22.95 ± 0.10 | 3.875 ± 0.017 | 4 |
| 23.08 ± 0.10 | 3.853 ± 0.017 | 4 |
| 23.94 ± 0.10 | 3.718 ± 0.015 | 1 |
| 24.25 ± 0.10 | 3.670 ± 0.015 | 1 |
| 24.60 ± 0.10 | 3.618 ± 0.015 | 18 |
| 25.27 ± 0.10 | 3.524 ± 0.014 | 6 |
| 25.52 ± 0.10 | 3.490 ± 0.013 | 6 |
| 25.71 ± 0.10 | 3.465 ± 0.013 | 32 |
| 26.04 ± 0.10 | 3.422 ± 0.013 | 8 |
| 26.69 ± 0.10 | 3.340 ± 0.012 | 6 |
| 27.03 ± 0.10 | 3.299 ± 0.012 | 2 |
| 27.25 ± 0.10 | 3.273 ± 0.012 | 3 |
| 27.65 ± 0.10 | 3.227 ± 0.011 | 2 |
| 27.81 ± 0.10 | 3.208 ± 0.011 | 4 |
| 28.11 ± 0.10 | 3.174 ± 0.011 | 12 |
| 28.48 ± 0.10 | 3.134 ± 0.011 | 8 |
| 28.63 ± 0.10 | 3.118 ± 0.011 | 4 |
| 29.85 ± 0.10 | 2.993 ± 0.010 | 3 |

XRPD data exhibited resolution of peaks indicative of crystalline material. The pattern was successfully indexed, indicating the sample is composed primarily of a single crystalline phase. The space group consistent with the assigned extinction symbol, as well as the unit cell parameters and derived quantities are tabulated in Table XV. Both P1 and P-1 are possible space groups for the unit cell of Form C. These space groups cannot be distinguished based on indexing alone. The indexed volume of 557.1 Å$^3$/Formula unit for Form C is significantly larger than the indexed volume of 489.5 Å$^3$/Formula unit for Form A. The difference of 67.6 Å$^3$/Formula unit is sufficient for approximately three moles of water or one half of a mole of toluene per formula unit.

TABLE XV

| Molecular Formula | $C_{19}H_{16}FN_5O$•HBr | | | | |
|---|---|---|---|---|---|
| Crystal System | Triclinic | | | | |
| Space Group | P1 or | a | 8.602 Å | α | 107.44° |
| | P-1 | b | 9.767 Å | β | 91.55° |
| | | c | 14.118 Å | γ | 98.96° |
| V | 1114.3 Å$^3$ | | | | |
| V/Z (Å$^3$/asym. unit) | 557.1 | | | | |
| Z'/Z | 2/2 or 1/2 | | | | |
| $D_c$ | 1.282 g/cm$^3$ | | | | |

Thermogravimetric data show a ~10 wt % loss between ~132° C. and ~253° C., likely associated with the loss of ~0.5 moles of toluene per mole of the HBr salt. Although indexing results indicate the possibility of the presence of toluene or water, the weight loss observed at this temperature range correlate better to the possibility of a toluene solvate. A sharp weight loss is observed at ~263° C., likely associated with decomposition. Vacuum drying of Form C at ~80° C. for about one day resulted in a mixture of Forms A and C.

The DSC thermogram shows a small broad endotherm with a peak maximum at ~222.4° C., likely associated with the loss of solvent observed from thermogravimetry. A strong sharp endotherm is observed at ~272.9° C., likely associated with the material melting concurrent with decomposition.

Proton nuclear magnetic resonance ($^1$H NMR) chemical shifts in the region ~7.0-8.5 ppm and integral values are overall consistent with a HBr salt of the compound of Formula I. The peaks at ~7.25, ~7.18, and ~2.31 ppm are attributable to ~0.4 moles of toluene per mole of the compound of Formula I. The peak at ~3.5 ppm is likely attributable to water.

Example 6

Characterization of Form E

Form E was characterized by X-ray powder diffraction (XRPD), thermogravimetry (TG), differential scanning calorimetry (DSC), moisture sorption analysis, proton nuclear magnetic resonance spectroscopy ($^1$H NMR), and elemental analysis. Form E was physically stable upon vacuum drying at ~60° C. for two days.

A representative XRPD pattern of crystalline Form E is shown in FIG. 3. Some XRPD peaks of crystalline Form E are summarized in Table XVI.

TABLE XVI

X-Ray Diffraction Peaks for Form E

| Two-theta angle (°) | d Space (Å) | Intensity (%) |
|---|---|---|
| 6.42 ± 0.10 | 13.762 ± 0.217 | 49 |
| 8.04 ± 0.10 | 10.992 ± 0.138 | 100 |
| 9.68 ± 0.10 | 9.136 ± 0.095 | 8 |
| 11.65 ± 0.10 | 7.594 ± 0.066 | 10 |
| 12.89 ± 0.10 | 6.868 ± 0.053 | 8 |
| 13.66 ± 0.10 | 6.483 ± 0.048 | 6 |
| 13.79 ± 0.10 | 6.421 ± 0.047 | 8 |
| 15.71 ± 0.10 | 5.639 ± 0.036 | 4 |
| 15.96 ± 0.10 | 5.551 ± 0.035 | 12 |
| 16.15 ± 0.10 | 5.489 ± 0.034 | 10 |
| 16.43 ± 0.10 | 5.394 ± 0.033 | 11 |
| 18.54 ± 0.10 | 4.786 ± 0.026 | 19 |
| 19.47 ± 0.10 | 4.558 ± 0.023 | 54 |
| 20.21 ± 0.10 | 4.394 ± 0.022 | 13 |
| 20.54 ± 0.10 | 4.323 ± 0.021 | 10 |
| 20.94 ± 0.10 | 4.241 ± 0.020 | 36 |
| 21.48 ± 0.10 | 4.137 ± 0.019 | 23 |
| 21.73 ± 0.10 | 4.090 ± 0.019 | 6 |
| 22.60 ± 0.10 | 3.935 ± 0.017 | 22 |
| 23.13 ± 0.10 | 3.845 ± 0.016 | 21 |
| 23.38 ± 0.10 | 3.804 ± 0.016 | 14 |
| 24.34 ± 0.10 | 3.657 ± 0.015 | 4 |
| 24.84 ± 0.10 | 3.585 ± 0.014 | 55 |
| 25.04 ± 0.10 | 3.556 ± 0.014 | 28 |
| 25.26 ± 0.10 | 3.526 ± 0.014 | 11 |
| 25.67 ± 0.10 | 3.470 ± 0.013 | 15 |
| 26.14 ± 0.10 | 3.409 ± 0.013 | 17 |
| 26.73 ± 0.10 | 3.336 ± 0.012 | 14 |
| 26.89 ± 0.10 | 3.315 ± 0.012 | 15 |
| 27.14 ± 0.10 | 3.285 ± 0.012 | 30 |
| 27.68 ± 0.10 | 3.223 ± 0.011 | 41 |
| 28.33 ± 0.10 | 3.150 ± 0.011 | 11 |
| 29.18 ± 0.10 | 3.060 ± 0.010 | 6 |
| 29.89 ± 0.10 | 2.990 ± 0.010 | 12 |

XRPD data exhibited resolution of peaks indicative of crystalline material. The pattern was successfully indexed, indicating the sample is composed primarily of a single crystalline phase. Space groups consistent with the assigned extinction symbol, unit cell parameters, and derived quantities are tabulated in Table XVII. The indexed volume of 448.1 Å$^3$ per formula unit for Form E is smaller than the indexed volume of 489.5 Å$^3$ per formula unit for Form A. The difference of 41.4 Å$^3$ per formula unit is sufficient for one mole of HBr per formula unit.

Thermogravimetric data show a ~11.9 wt % loss between ~26° C. and ~81° C., likely associated with the release of surface water. An additional ~2.1 wt % loss is observed between ~100° C. and ~182° C., possibly attributable to the release of ~0.5 moles of water or ~0.1 moles of dimethylformamide. A sharp weight loss occurs at ~227° C., likely associated with decomposition.

The DSC thermogram exhibited a sharp endotherm at ~2.0° C. followed by a broad endotherm at ~75.3° C., likely associated with residual water melting followed by the release of residual water. A strong endotherm at ~173.6° C. may be attributed to the material melting. A new material recrystallizes from the melt as suggested by the exotherm at ~185.9° C. and then proceeds to melt as indicated by the sharp endotherm at ~200.8° C.

Moisture sorption data are consistent with a limited hygroscopic material. Data show a ~0.2 wt % loss upon equilibration at ~5% RH. A 0.6 wt % gain is observed between ~5% and ~95% RH. A ~0.6 wt % loss was observed upon decreasing the relative humidity to ~5% RH.

TABLE XVII

| Molecular Formula | $C_{19}H_{16}FN_5O \cdot HBr$ (HBr salt) |
|---|---|
| | $C_{19}H_{16}FN_5O$ (Free base) |
| Crystal System | Orthorhombic |
| Space Group | a   7.166 Å   α   90° |
| | b   18.223 Å   β   90° |
| | c   27.449 Å   γ   90° |
| V | 3584.5 Å$^3$ |
| V/Z (Å$^3$/asym. unit) | 448.1 |
| Z'/Z | 2/8 or 1/8 |
| $D_c$ | 1.59 g/cm$^3$ (HBr salt) |
| | 1.29 g/cm$^3$ (free base) |

Elemental analysis, however, does indicate the presence of bromide, although at approximately half the expected percentage if the 1:1 salt was still intact (Predicted values for $C_{19}H_{17}BrFN_5O$: C, 53.04%, H, 3.98%, N, 16.28%, Br: 18.57%; Predicted values for $C_{19}H_{16.5}Br_{0.5}FN_5O$: C, 58.54%, H, 4.27%, N, 17.97%, Br: 10.25%; Experimental values: C, 57.05%, H, 4.32%, N, 17.54%, Br: 9.46%). The experimental values for carbon, nitrogen, and hydrogen are higher than that predicted for a 1:1 hydrobromide salt but lower than for the free base.

Example 7

Characterization of Form B, D, and F

Forms B, D, and F were characterized by X-ray powder diffraction (XRPD). Vacuum drying at ~60° C. of Form B isolated for about 1 day resulted in a mixture of Form A with small amount of Form B. Vacuum drying at ~40° C. of Form D isolated for about 3 days resulted in Form A.

Figure 4:
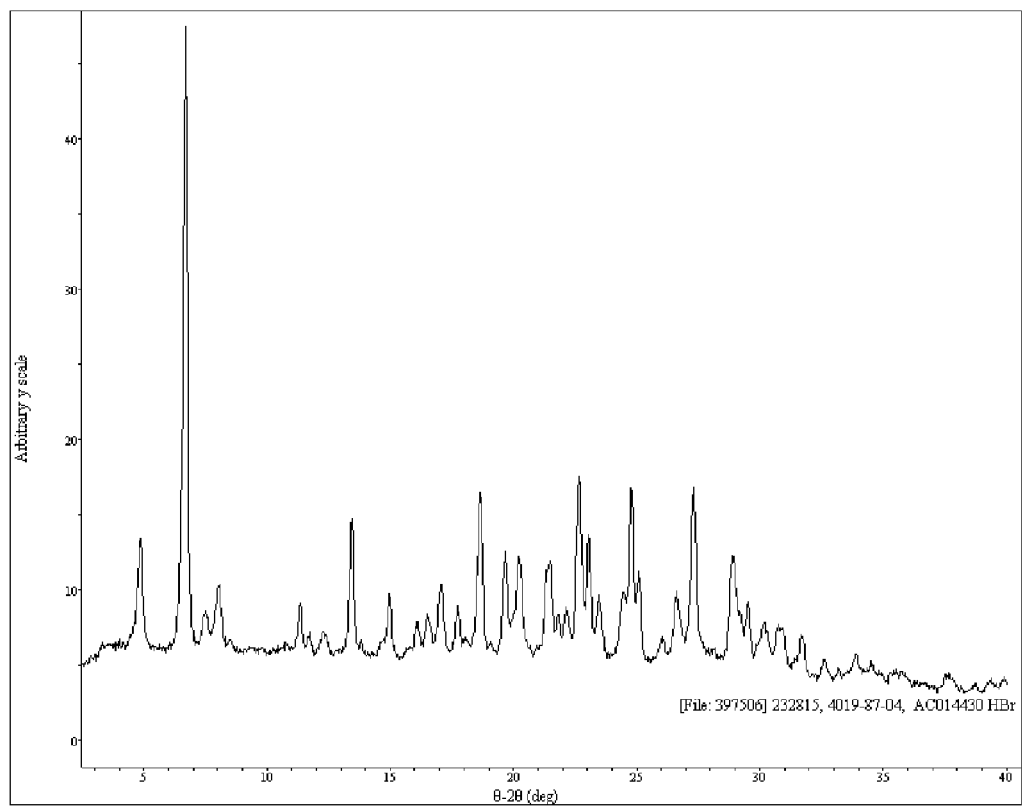
FIG. 4 depicts an X-ray powder (XRP) diffractogram of a hydrobromide salt of (4-fluorophenyl)(4-(5-methyl-1H-pyrazol-3-ylamino)quinazolin-2-yl)methanol in crystalline Form B.
Figure 5:
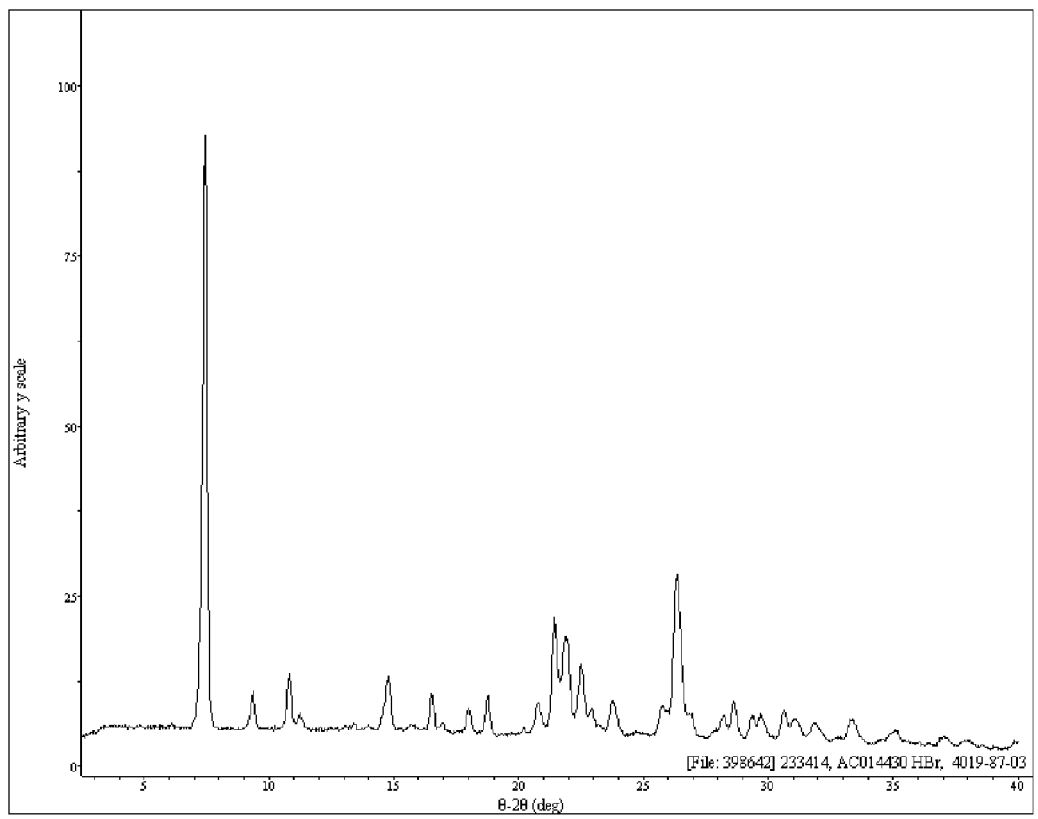
FIG. 5 depicts an X-ray powder (XRP) diffractogram of a hydrobromide salt of (4-fluorophenyl)(4-(5-methyl-1H-pyrazol-3-ylamino)quinazolin-2-yl)methanol in crystalline Form D.
Figure 6:
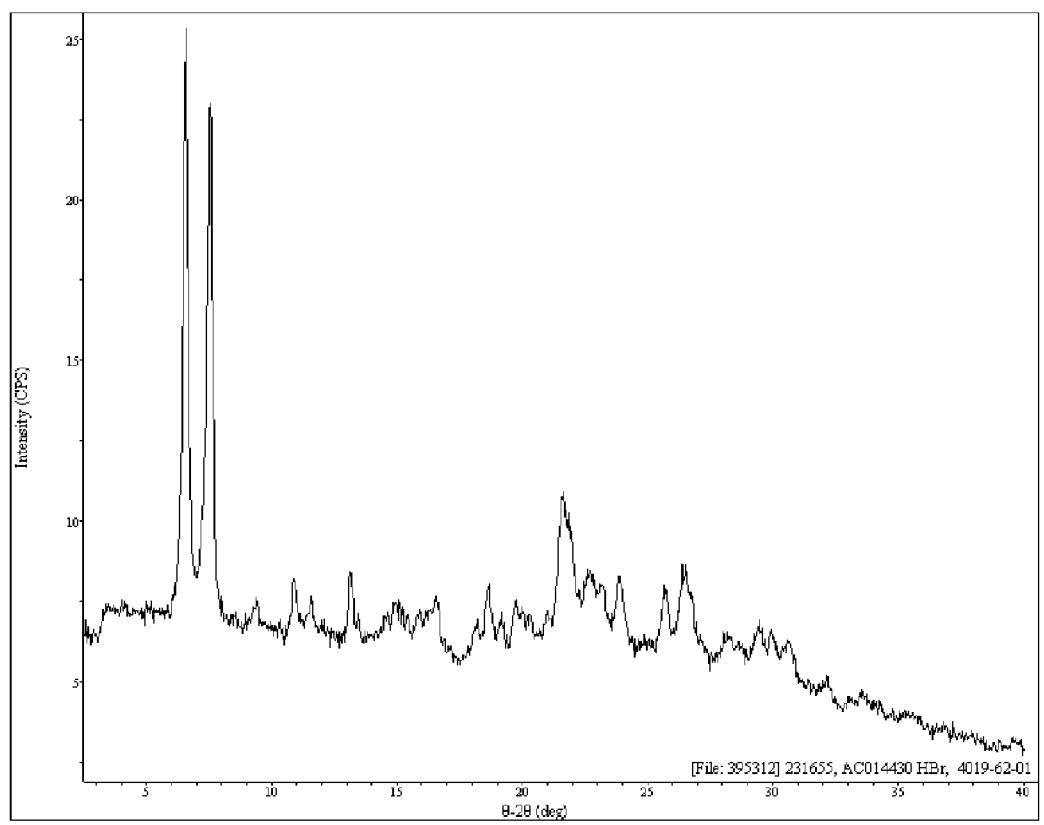
FIG. 6 depicts an X-ray powder (XRP) diffractogram of a hydrobromide salt of (4-fluorophenyl)(4-(5-methyl-1H-pyrazol-3-ylamino)quinazolin-2-yl)methanol in crystalline Form F.

Representative XRPD patterns for crystalline Forms B, D, and F are shown in FIGS. 4, 5, and 6, respectively. For Form B, as shown in FIG. 4, the peak at 7.47° 2θ may be attributable to the presence of Form A as an additional phase in the material. For Form F, FIG. 6 represents an XRPD pattern of a mixture of Forms and F, where the peaks due to Form A were to be subtracted. Some XRPD peaks of crystalline Forms B, D, and F are summarized in Table XVIII, XIX, and XX, respectively.

TABLE XVIII

X-Ray Diffraction Peaks for Form B

| Two-theta angle (°) | d Space (Å) | Intensity (%) |
|---|---|---|
| 4.86 ± 0.10 | 18.183 ± 0.382 | 18 |
| 6.69 ± 0.10 | 13.213 ± 0.200 | 100 |
| 7.47 ± 0.10 | 11.835 ± 0.160 | 6 |
| 8.01 ± 0.10 | 11.038 ± 0.139 | 10 |
| 8.46 ± 0.10 | 10.452 ± 0.125 | 2 |
| 11.34 ± 0.10 | 7.803 ± 0.069 | 8 |
| 11.70 ± 0.10 | 7.564 ± 0.065 | 4 |
| 12.27 ± 0.10 | 7.214 ± 0.059 | 4 |
| 13.41 ± 0.10 | 6.603 ± 0.049 | 22 |
| 13.80 ± 0.10 | 6.417 ± 0.047 | 3 |
| 14.64 ± 0.10 | 6.051 ± 0.041 | 3 |
| 14.94 ± 0.10 | 5.930 ± 0.040 | 10 |
| 16.08 ± 0.10 | 5.512 ± 0.034 | 6 |
| 16.50 ± 0.10 | 5.373 ± 0.033 | 6 |
| 17.04 ± 0.10 | 5.204 ± 0.030 | 11 |
| 17.70 ± 0.10 | 5.011 ± 0.028 | 7 |

TABLE XVIII-continued

X-Ray Diffraction Peaks for Form B

| Two-theta angle (°) | d Space (Å) | Intensity (%) |
|---|---|---|
| 18.63 ± 0.10 | 4.763 ± 0.025 | 26 |
| 19.05 ± 0.10 | 4.659 ± 0.024 | 2 |
| 19.65 ± 0.10 | 4.518 ± 0.023 | 16 |
| 20.22 ± 0.10 | 4.392 ± 0.022 | 15 |
| 21.39 ± 0.10 | 4.154 ± 0.019 | 14 |
| 21.81 ± 0.10 | 4.075 ± 0.019 | 7 |
| 22.11 ± 0.10 | 4.021 ± 0.018 | 8 |
| 22.65 ± 0.10 | 3.926 ± 0.017 | 29 |
| 23.04 ± 0.10 | 3.860 ± 0.017 | 19 |
| 23.43 ± 0.10 | 3.797 ± 0.016 | 9 |
| 24.45 ± 0.10 | 3.641 ± 0.015 | 11 |
| 24.75 ± 0.10 | 3.597 ± 0.014 | 27 |
| 25.08 ± 0.10 | 3.551 ± 0.014 | 13 |
| 25.98 ± 0.10 | 3.430 ± 0.013 | 4 |
| 26.61 ± 0.10 | 3.350 ± 0.012 | 11 |
| 27.27 ± 0.10 | 3.270 ± 0.012 | 28 |
| 28.89 ± 0.10 | 3.091 ± 0.011 | 18 |
| 29.16 ± 0.10 | 3.063 ± 0.010 | 9 |
| 29.49 ± 0.10 | 3.029 ± 0.010 | 10 |

TABLE XIX

X-Ray Diffraction Peaks for Form D

| Two-theta angle (°) | d Space (Å) | Intensity (%) |
|---|---|---|
| 7.41 ± 0.10 | 11.930 ± 0.163 | 100 |
| 9.33 ± 0.10 | 9.479 ± 0.102 | 7 |
| 10.80 ± 0.10 | 8.192 ± 0.076 | 10 |
| 11.19 ± 0.10 | 7.907 ± 0.081 | 3 |
| 14.76 ± 0.10 | 6.002 ± 0.041 | 10 |
| 15.72 ± 0.10 | 5.637 ± 0.036 | 1 |
| 16.50 ± 0.10 | 5.373 ± 0.033 | 7 |
| 16.92 ± 0.10 | 5.240 ± 0.031 | 2 |
| 17.97 ± 0.10 | 4.936 ± 0.027 | 4 |
| 18.75 ± 0.10 | 4.733 ± 0.025 | 7 |
| 20.19 ± 0.10 | 4.398 ± 0.022 | 1 |
| 20.76 ± 0.10 | 4.279 ± 0.020 | 5 |
| 21.42 ± 0.10 | 4.418 ± 0.019 | 20 |
| 21.84 ± 0.10 | 4.070 ± 0.018 | 17 |
| 22.47 ± 0.10 | 3.957 ± 0.017 | 12 |
| 22.89 ± 0.10 | 3.885 ± 0.017 | 5 |
| 23.76 ± 0.10 | 3.745 ± 0.016 | 6 |
| 25.74 ± 0.10 | 3.461 ± 0.013 | 5 |
| 26.31 ± 0.10 | 3.387 ± 0.013 | 28 |
| 26.85 ± 0.10 | 3.321 ± 0.012 | 4 |
| 28.20 ± 0.10 | 3.165 ± 0.011 | 4 |
| 28.59 ± 0.10 | 3.122 ± 0.011 | 6 |
| 29.34 ± 0.10 | 3.044 ± 0.010 | 4 |
| 29.67 ± 0.10 | 3.011 ± 0.010 | 4 |

TABLE XX

X-Ray Diffraction Peaks for Form F

| Two-theta angle (°) | d Space (Å) | Intensity (%) |
|---|---|---|
| 6.57 ± 0.10 | 13.454 ± 0.208 | 100 |

Example 8

Phase I clinical study of racemic (4-fluorophenyl)(4-((5-methyl-1H-pyrazol-3-yl)amino)quinazolin-2-yl)methanol Phase I clinical study of racemic (4-fluorophenyl)(4-((5-methyl-1H-pyrazol-3-yl)amino)quinazolin-2-yl)methanol HBr salt was performed in volunteers in a double-blind, placebo-controlled, three-part study. In part one, subjects received a single oral dose ranging from 60-750 mg/day of the racemate. In part two, subjects received a QD dose ranging from 240-720 mg/day of the racemate for 14 days continuously. In one cohort of part two study, BID dose of 360 mg of the racemate for 14 days continuously (for a total 720 mg/day). In part three, a randomized, open-label, two-sequence, two-period, crossover food effect following a single dose was studied. For all parts of the study, PK parameters were evaluated in plasma and in parts one and two, in urine, for racemic (4-fluorophenyl)(4-((5-methyl-1H-pyrazol-3-yl)amino)quinazolin-2-yl)methanol, including chiral analysis of its R and S enantiomers. The following PK parameters were computed from plasma concentration data: area under the plasma concentration-time curve from time 0 to time of last quantifiable concentration ($AUC_{0-\tau}$), area under the plasma concentration-time curve from time 0 to infinity ($AUC_{0-\infty}$), maximum observed plasma concentration ($C_{max}$), time to reach $C_{max}$ ($t_{max}$), terminal elimination rate constant ($\lambda z$), terminal half-life ($t_{1/2}$), apparent clearance after extravascular administration (CL/F), and apparent volume of distribution during the terminal phase after extravascular administration (Vz/F). For urine collection data, the following parameters were calculated: total amount of drug excreted in urine from time 0 to 48 hours ($Ae_{0-48}$) and fraction of drug excreted in urine (Fe). The study was also designed to assess the safety, tolerability and pharmacodynamic effects of the single and multiple oral doses of racemic (4-fluorophenyl)(4-((5-methyl-1H-pyrazol-3-yl)amino)quinazolin-2-yl)methanol on human subjects. The pharmacodynamic effects are based on measurement of STAT phosphorylation levels following ex vivo stimulation with cytokines signaling through JAK2 and JAK1. Also for part two of the study only, flow cytometry was performed to determine the prevalence of cellular subsets as identified by cell-type specific cell surface markers.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A crystalline hydrobromide salt of (4-fluorophenyl)(4-(5-methyl-1H-pyrazol-3-ylamino)quinazolin-2-yl)methanol, having an X-ray powder diffraction pattern with a peak expressed in two-theta at approximately 7.5. 10.8, or 14.8°.

2. The hydrobromide salt of claim 1, having an endotherm with a peak temperature of about 274° C. in a differential scanning calorimetry thermogram.

3. The hydrobromide salt of claim 1, having a weight loss of no greater than about 1% between about 25 to about 114° C. or no greater than about 1% between about 142 to about 218° C. in a thermogravimetric thermogram.

4. The hydrobromide salt of claim 1, wherein the hydrobromide salt is non-hygroscopic.

5. The hydrobromide salt of claim 4, having a mass gain of no greater than about 1% in response to an increase in humidity from about 5% to about 95% relative humidity at 25° C. or a mass loss of no greater than about 1% in response to a decrease in humidity from about 95% to about 5% relative humidity at 25° C.

6. The hydrobromide salt of claim 1, having unit cell dimensions of: a=8.6 Å, b=9.8 Å, c=12.6 Å, α=77°, β=73°, and γ=84°.

7. A crystalline hydrobromide salt of (4-fluorophenyl)(4-(5-methyl-1H-pyrazol-3-ylamino)quinazolin-2-yl)methanol, having an X-ray powder diffraction pattern with a peak expressed in two-theta at approximately 4.9, 6.7, or 18.6°.

8. A crystalline hydrobromide salt of (4-fluorophenyl)(4-(5-methyl-1H-pyrazol-3-ylamino)quinazolin-2-yl)methanol, having an X-ray powder diffraction pattern with a peak expressed in two-theta at approximately 6.6 or 18.4°.

9. The hydrobromide salt of claim 8, having an endotherm with a peak temperature of about 222 or about 273° C. in a differential scanning calorimetry thermogram.

10. The hydrobromide salt of claim 8, having a weight loss of about 10% between about 132 and 253° C. in a thermogravimetric thermogram.

11. The hydrobromide salt of claim 8, having unit cell dimensions of: a=8.6 Å, b=9.8 Å, c=14.1 Å, α=107°, β=92°, and γ=99°.

12. A crystalline hydrobromide salt of (4-fluorophenyl)(4-(5-methyl-1H-pyrazol-3-ylamino)quinazolin-2-yl)methanol, having an X-ray powder diffraction pattern with a peak expressed in two-theta at approximately 7.4, 10.8, or 14.8°.

13. A crystalline hydrobromide salt of (4-fluorophenyl)(4-(5-methyl-1H-pyrazol-3-ylamino)quinazolin-2-yl)methanol, having an X-ray powder diffraction pattern with a peak expressed in two-theta at approximately 6.4, 8.0, 11.7, or 19.5°.

14. The hydrobromide salt of claim 13, having an endotherm with a peak temperature of about 76, about 174, or about 201° C. or an exotherm with a peak temperature of about 186° C. in a differential scanning calorimetry thermogram.

15. The hydrobromide salt of claim 13, having a weight loss of about 12% between about 26 and about 81° C. or about 2% between about 100 and about 182° C. in a thermogravimetric thermogram.

16. The hydrobromide salt of claim 13, wherein the hydrobromide salt is non-hygroscopic.

17. The hydrobromide salt of claim 16, having a mass gain of no greater than about 1% in response to an increase in humidity from about 5% to about 95% relative humidity at 25° C. or a mass loss of no greater than about 1% in response to a decrease in humidity from about 95% to about 5% relative humidity at 25° C.

18. The hydrobromide salt of claim 13, having unit cell dimensions of: a=7.2 Å, b=18.2 Å, c=27.4 Å, α=90°, β=90°, and γ=90°.

19. A crystalline hydrobromide salt of (4-fluorophenyl)(4-(5-methyl-1H-pyrazol-3-ylamino)quinazolin-2-yl)methanol, having an X-ray powder diffraction pattern with a peak expressed in two-theta at approximately 6.6°.

20. A pharmaceutical composition comprising the salt of claim 1, and a pharmaceutically acceptable excipient.

21. The pharmaceutical composition of claim 20, wherein the composition is formulated for oral, nasal, bronchial, or topical administration.

22. The pharmaceutical composition of claim 20, wherein the composition is formulated as a single dosage form.

23. The pharmaceutical composition of claim 20, wherein the composition is formulated as oral, parenteral, or intravenous dosage form.

24. The pharmaceutical composition of claim 23, wherein the oral dosage form is a tablet or capsule.

25. The hydrobromide salt of claim 1, having an X-ray powder diffraction pattern substantially as shown in FIG. 1.

26. The hydrobromide salt of claim 8, having an X-ray powder diffraction pattern substantially as shown in FIG. 2.

27. The hydrobromide salt of claim 13, having an X-ray powder diffraction pattern substantially as shown in FIG. 3.

* * * * *